(12) United States Patent
Stein

(10) Patent No.: US 11,491,100 B2
(45) Date of Patent: *Nov. 8, 2022

(54) DERMAL COMPOSITION COMPRISING CHELATOR AND BASE

(71) Applicant: Primal Therapies, Inc., Minneapolis, MN (US)

(72) Inventor: Emily A. Stein, Minneapolis, MN (US)

(73) Assignee: Primal Therapies, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/144,657

(22) Filed: Sep. 27, 2018

(65) Prior Publication Data

US 2019/0262255 A1     Aug. 29, 2019

Related U.S. Application Data

(63) Continuation of application No. 14/775,959, filed as application No. PCT/US2014/024613 on Mar. 12, 2014, now Pat. No. 10,117,823.

(60) Provisional application No. 61/965,678, filed on Feb. 5, 2014, provisional application No. 61/851,748, filed on Mar. 12, 2013.

(51) Int. Cl.
| | |
|---|---|
| *A61K 47/40* | (2006.01) |
| *A61K 31/724* | (2006.01) |
| *A61K 31/195* | (2006.01) |
| *A61Q 19/00* | (2006.01) |
| *A61P 31/04* | (2006.01) |
| *A61P 29/00* | (2006.01) |
| *A61K 8/73* | (2006.01) |
| *A61K 8/365* | (2006.01) |
| *A61K 8/41* | (2006.01) |
| *A61K 8/44* | (2006.01) |
| *A61K 8/49* | (2006.01) |
| *A61K 8/55* | (2006.01) |
| *A61K 8/64* | (2006.01) |
| *A61K 8/66* | (2006.01) |
| *A61K 8/67* | (2006.01) |
| *A61Q 17/00* | (2006.01) |
| *A61K 8/11* | (2006.01) |
| *A61K 8/19* | (2006.01) |
| *A61Q 11/00* | (2006.01) |
| *A61K 9/00* | (2006.01) |

(52) U.S. Cl.
CPC ............... *A61K 8/738* (2013.01); *A61K 8/11* (2013.01); *A61K 8/19* (2013.01); *A61K 8/365* (2013.01); *A61K 8/41* (2013.01); *A61K 8/44* (2013.01); *A61K 8/4926* (2013.01); *A61K 8/55* (2013.01); *A61K 8/64* (2013.01); *A61K 8/66* (2013.01); *A61K 8/67* (2013.01); *A61K 8/73* (2013.01); *A61Q 11/00* (2013.01); *A61Q 17/005* (2013.01); *A61K 9/0063* (2013.01); *A61K 2800/51* (2013.01); *A61K 2800/592* (2013.01)

(58) Field of Classification Search
CPC ...... A61K 2300/00; A61K 9/08; A61K 47/40; A61K 9/0014; A61K 47/183; A61K 38/00; A61K 45/06; A61K 33/00; A61K 31/724; A61K 31/4415; A61K 8/35; A61K 2800/51; A61K 8/64; A61K 47/6951; A61K 2039/572; A61K 2800/10; A61K 8/738; A61Q 19/00; A61Q 17/005
See application file for complete search history.

(56) References Cited

U.S. PATENT DOCUMENTS

| | | | |
|---|---|---|---|
| 3,558,769 | A | 1/1971 | Globus |
| 4,267,166 | A | 5/1981 | Yajima |
| 4,339,432 | A | 7/1982 | Ritchey et al. |
| 4,728,510 | A | 3/1988 | Shibanai et al. |
| 4,732,759 | A | 3/1988 | Shibanai et al. |
| 4,980,165 | A | 12/1990 | Isaacs et al. |
| 5,389,685 | A | 2/1995 | Smith et al. |
| 5,668,097 | A | 9/1997 | Trinh et al. |
| 5,780,020 | A | 7/1998 | Peterson et al. |
| 5,985,296 | A | 11/1999 | Moldenhauer et al. |

(Continued)

FOREIGN PATENT DOCUMENTS

| | | |
|---|---|---|
| CN | 1158559 A | 9/1997 |
| CN | 1223097 A | 7/1999 |

(Continued)

OTHER PUBLICATIONS

Artiss, J.D. et al. (2006). "The effects of a new soluble dietary fiber on weight gain and selected blood parameters in rats," Metabolism 55:195-202.

Atanasova, N. et al. (2008). "Isolation of novel alkaliphilic bacillus strains for cyclodextrin glucanotransferase production," Appl. Biochem. Biotechnol. 149:155-167.

Azarpazhooh, A. et al. (2006). "Systematic review of the association between respiratory diseases and oral health," J. Periodontal. 77:1465-1482.

(Continued)

*Primary Examiner* — Tracy Liu

(74) *Attorney, Agent, or Firm* — Cooley LLP

(57) ABSTRACT

The present invention relates to non-toxic consumable compositions and formulations comprising chelator and base having synergistic effects on microbial metabolism and/or growth and/or pathogenic effectors and their use to promote and maintain health in mammals. The current invention also relates to non-toxic consumable compositions comprising more than one chelator and/or more than one base. The present invention further relates to methods for selecting said chelator and base composition and methods for detecting conditions in which selected compositions may be used. The present invention relates to the synergistic compositions and methods of their use for maintaining health, promoting health and treating diseases.

19 Claims, 8 Drawing Sheets

(56) References Cited

U.S. PATENT DOCUMENTS

| | | | |
|---|---|---|---|
| 5,998,488 | A | 12/1999 | Shinohara et al. |
| 6,043,259 | A | 3/2000 | Dhalla et al. |
| 6,261,540 | B1 | 7/2001 | Nelson |
| 7,838,485 | B2 | 11/2010 | Heisig et al. |
| 7,939,061 | B2 | 5/2011 | Prakash et al. |
| 7,960,430 | B2 | 6/2011 | Wirth et al. |
| 10,117,823 | B2 | 11/2018 | Stein |
| 2002/0091074 | A1 | 7/2002 | Wooley et al. |
| 2003/0232040 | A1 | 12/2003 | Beckman et al. |
| 2004/0076591 | A1 | 4/2004 | Anthony Nelson et al. |
| 2004/0265435 | A1 | 12/2004 | Kurauchi et al. |
| 2005/0085444 | A1 | 4/2005 | Archambault et al. |
| 2005/0136086 | A1 | 6/2005 | Herruzo et al. |
| 2006/0045855 | A1 | 3/2006 | Sasson |
| 2006/0052353 | A1* | 3/2006 | Johnson ............ A61K 31/573 514/178 |
| 2006/0134020 | A1 | 6/2006 | Robinson et al. |
| 2008/0008727 | A1* | 1/2008 | Fredon ............... A61K 8/368 424/401 |
| 2009/0203628 | A1* | 8/2009 | Marini ............... A61Q 19/00 514/1.1 |
| 2009/0209604 | A1* | 8/2009 | Zhang ............... A61K 9/0014 514/390 |
| 2009/0215727 | A1 | 8/2009 | Douglas |
| 2009/0238820 | A1 | 9/2009 | Allan et al. |
| 2009/0258841 | A1* | 10/2009 | Murphy ............... A61K 8/55 514/125 |
| 2010/0034923 | A1 | 2/2010 | Daeschel et al. |
| 2010/0087392 | A1 | 4/2010 | Freiss et al. |
| 2011/0020328 | A1 | 1/2011 | Brisbane et al. |
| 2011/0166105 | A1 | 7/2011 | Farng et al. |
| 2011/0280943 | A1* | 11/2011 | Mansouri ............ A61K 8/27 424/489 |
| 2016/0030327 | A1 | 2/2016 | Stein |

FOREIGN PATENT DOCUMENTS

| | | |
|---|---|---|
| CN | 1688322 A | 10/2005 |
| CN | 101119702 A | 2/2008 |
| CN | 102845422 A | 1/2013 |
| CN | 102988223 A | 3/2013 |
| CN | 103127021 A | 6/2013 |
| DE | 3203274 A1 | 10/1982 |
| DE | 19615820 A1 | 10/1997 |
| DE | 10340684 A1 | 7/2004 |
| DE | 102005023301 A1 | 11/2006 |
| EP | 1 291 460 A1 | 3/2003 |
| EP | 1 718 658 A1 | 11/2006 |
| EP | 2 043 451 A1 | 4/2009 |
| FR | 1 458 094 A | 3/1966 |
| FR | 2 876 914 A1 | 4/2006 |
| JP | H04-13741 A | 1/1992 |
| JP | H09-235209 A | 9/1997 |
| JP | 2002-037884 A | 2/2002 |
| JP | 2003089641 A | 3/2003 |
| JP | 2007-161642 A | 6/2007 |
| JP | 2009-249499 A | 10/2009 |
| RO | 111151 B1 | 7/1996 |
| WO | WO-96/09029 A1 | 3/1996 |
| WO | WO-96/40262 A2 | 12/1996 |
| WO | WO-96/40262 A3 | 12/1996 |
| WO | WO-98/31332 A1 | 7/1998 |
| WO | WO-03/063805 A2 | 8/2003 |
| WO | WO-03/063805 A3 | 8/2003 |
| WO | WO-03/101415 A1 | 12/2003 |
| WO | WO-2004/056346 A1 | 7/2004 |
| WO | WO-2004/028461 A2 | 8/2004 |
| WO | WO-2004/028461 A3 | 8/2004 |
| WO | WO-2005/099655 A2 | 10/2005 |
| WO | WO-2005/099655 A3 | 10/2005 |
| WO | WO-2006/068753 A1 | 6/2006 |
| WO | WO-2008/008975 A2 | 1/2008 |
| WO | WO-2008/087034 A2 | 7/2008 |
| WO | WO-2008/087034 A3 | 7/2008 |
| WO | WO-2009/020398 A2 | 2/2009 |
| WO | WO-2009/020398 A3 | 2/2009 |
| WO | WO-2009/105786 A2 | 8/2009 |
| WO | WO-2009/105786 A3 | 8/2009 |
| WO | WO-2011/162756 A1 | 12/2011 |
| WO | WO-2012/090018 A1 | 7/2012 |
| WO | WO-2012/154739 A1 | 11/2012 |
| WO | WO-2013/036286 A2 | 3/2013 |
| WO | WO-2013/036286 A3 | 3/2013 |
| WO | WO-2013/155485 A2 | 10/2013 |
| WO | WO-2013/155485 A3 | 10/2013 |
| WO | WO-2014/159659 A1 | 10/2014 |

OTHER PUBLICATIONS

Azarpazhooh, A. et al. (2011). "Xylitol for preventing acute otitis media in children up to 12 years of age," Cochrane Database Systematic Reviews 9;(11):CD007095, 47 total pages.

Balin, B.J. et al. (2001). "Role of infection in Alzheimer's disease," JAOA 101:S1-S6.

Baddour et al. Circulation Jun. 14, 2005, vol. 111, pp. 394-434, "Infective Endocarditis. Diagnosis, Antimicrobial Therapy, and Management of Complications. A Statement for Healthcare Professionals From the Committee on Rheumatic Fever, Endocarditis, and Kawasaki Disease, Council on Cardiovascular Disease in the Young, and the Councils on Clinical Cardiology, Stroke, and Cardiovascular Surgery and Anesthesia, American Heart Association".

Banks, J. et al. (2002). "*Streptococcus sanguis* secretes CD14-binding proteins that stimulate cytokine synthesis: a clue to the pathogenesis of infective (bacterial) endocarditis?" Microb. Pathog. 32:105-116.

Bar, R. et al. (1994). "Bacterial toxicity of cyclodextrins: luminuous *Escherichia coli* as a model," Appl. Microbiol. Biotechnol. 41:574-577.

Barts, P.W.J.A. et al. (1980). "Uptake of the lipophilic cation dibenzyldimethylammonium into *Saccharomyces cerevisiae*. Interaction with the thiamine transport system," Biochim. Biophys. Acta. 597:125-136.

Bassim, C.W. et al. (2008). "Modification of the risk of mortality from pneumonia with oral hygiene care," J. Am. Geriatr. Soc. 56:1601-1607.

Beck, J.D. et al. (1996). "Epidemiology of periodontal diseases," Curr. Opin. Periodontol. 3:3-9.

Beck, J.D. (1998). "Periodontitis: a risk factor for coronary heart disease?" Ann. Periodontol. 3:127-141.

Bek-Thomsen et al. Journal of Clinical Microbiology Oct. 2008, vol. 46, No. 10, pp. 3355-3360, "Acne is Not Associated with Yet-Uncultured Bacteria".

Belhorn, L.R. et al. (1993). "Erosive osteoarthritis," Semin. Arthritis Rheum. 22:298-306.

Berger, A. et al. (1984). "More on neuropathy from pyridoxine abuse," N. Engl. J. Med. 311:986-987.

Berlin, R. et al. (1968). "Secretion of purines by the small intestine: general characteristics," Am J Physiol. 215(4):932-41.

Bernstein, A.L. (1990). "Vitamin B6 in clinical neurology," Ann. NY Acad. Sci. 585:250-260.

Bollen et al. International Journal of Oral Science 2012, vol. 4, p. 55-63, "Halitosis: the multidisciplinary approach".

Borodi, G. et al. (2008). "Spectroscopic investigations and crystal structure from synchrotron powder data of the inclusion complex of beta-cyclodextrin with atenolol," Spectrochim. Acta A Mol. Biomol. Spectrosc. 70:1041-1048.

Bowden, G.H. et al. (1990). "Association of selected bacteria with the lesions of root surface caries," Oral Microbiol. Immunol. 5:346-351.

Braud, A. et al. (2009). "Enhanced phytoextraction of an agricultural Cr- and Pb-contaminated soil by bioaugmentation with siderophore-producing bacteria," Chemosphere 74:280-286.

Braud, A. et al. (2009). "The pseudomonas aeruginosa pyochelin-iron uptake pathway and its metal specificity," J. Bacteriology 191:3517-3525.

(56) References Cited

OTHER PUBLICATIONS

Bretz, W.A. et al. (2005). "Systemic inflammatory markers, periodontal diseases, and periodontal infections in an elderly population," J. Am. Geriatr. Soc. 53:1532-1537.
Brook, I. (2011). "Microbiology of sinusitis," Proc. Am. Thorac. Soc. 8:90-100.
Brown et al. (1988). Journal of Antimicrobial Chemotherapy vol. 22, p. 777-783, "Leading Articles".
Buvat, J. et al. (1998). "Double-blind multicenter study comparing alprostadil α-cyclodextrin with moxisylyte chlorhydrate in patients with chronic erectile dysfunction," J. Urol. 159:116-119.
Califano, J.V. et al. (1996). "Influence of anti-Actinobacillus actinomycetemcomitans Y4 (serotype b) lipopolysaccharide on severity of generalized early-onset periodontitis," Infect. Immun. 64:3908-3910.
Carrano, C.J. et al. (1996). "Coordination chemistry of the carboxylate type siderophore rhizoferrin: The iron(III) complex and its metal analogs," Inorg. Chem. 35:6429-6436.
Carrano, C.J. et al. (1996). "Fungal ferritins: the ferritin from mycelia of Absidia spinosa is a bacterioferritin," FEBS Letters 390:261-264.
Carvalho, M.D. et al. (2004). "Impact of mouthrinses on morning bad breath in healthy subjects," J. Clin. Periodontol. 31:85-90.
Castro-Hermida, J.A. et al. (2004). "Efficacy of alpha-cyclodextrin against experimental cryptosporidiosis in neonatal goats," Vet Parasitol. 120:35-41.
Caufield et al. Caries Research 2007, vol. 41, pp. 2-8, "Diversity of Lactobacilli in the Oral Cavities of Young Women with Dental Caries".
Cavallo, T. et al. (1990). "Bacterial lipopolysaccharide transforms mesangial into proliferative lupus nephritis without interfering with processing of pathogenic immune complexes in NZB/W mice," Am J Pathol. 137(4):971-8.
Chalmers, J.M. et al. (2005). "A systematic review of oral health assessment by nurses and carers for residents with dementia in residential care facilities," Spec. Care Dentist 25:227-233.
Chaturvedi, K. et al. (2011). "Cyclodextrin-based siRNA delivery nanocarriers: a state-of-the-art review," Expert Opin. Drug Deliv. 8:1455-1468.
Chen, L.M. et al. (1998). "Fe chelates from compost microorganisms improve Fe nutrition of soybean and oat," Plant and Soil 200:139-147.
Chu, C.H. et al. (2011). "Oral health of Chinese people with systemic sclerosis," Clin. Oral Invest. 15:931-939.
Clark, D.C. (1991). "Current research in preventive dentistry and its impact on the future of dental care," J. Can. Dent. Assoc. 57:561-564.
Cohen, H. et al. (1958). "Hodgkin's disease (familial) associated with multiple malignant neoplasms," Cancer 11:1247-1254.
Colombo, A.V. et al. (2006). "Identification of oral bacteria associated with crevicular epithelial cells from chronic periodontitis lesions," J. Med. Microbiol. 55:609-615.
Cummings, J.L. et al. (1998). "Panel discussion," Neurology 51 (Suppl. 1):S2-S17; Discussion S65-S67.
D'Aiuto, F. et al. (2004). "Periodontitis and systemic inflammation: control of the local infection is associated with a reduction in serum inflammatory markers," J Dent Res. 83(2):156-60.
Debouzy, J.C. et al. (1998). "Mechanism of α-cyclodextrin induced hemolysis. 2. A study of the factors controlling the association with serine-, ethanolamine-, and choline-phospholipids," J. Pharm. Sci. 87:59-66.
Dalton, K. et al. (1987). "Characteristics of pyridoxine overdose neuropathy syndrome," Acta Neurol. Scand. 76:8-11.
De Bie, A.T.H.J. et al. (1998). "Disposition of [14C]γ-cyclodextrin in germ-free and conventional rats," Regul. Toxicol. Pharmacol. 27:150-158.
Dehkordi, L.S. et al. (2008). "Basic 3-hydroxypyridin-4-ones: potential antimalarial agents," Eur. J. Med. Chem. 43:1035-1047.
Del Tredici, K. et al. (2010). "Lewy pathology in the submandibular gland of individuals with incidental Lewy body disease and sporadic Parkinson's disease," Acta Neuropathol. 119:703-713.
Del Valle, E.M.M. (2004). "Cyclodextrins and their uses: A review," Process Biochem. 39(9):1033-1046.
Demmer et al. J. Clin Periodontol. Nov. 2011, vol. 38, No. 11 , p. 998-1006, "Periodontal Disease, Tooth Loss and Incident Rheumatoid Arthritis: Results from the First National Health and Nutrition Examination Survey and its Epidemiologic Follow-up Study".
Demmer, R.T. et al. (2008). "Periodontal disease and incident type 2 diabetes: results from the First National Health and Nutrition Examination Survey and its epidemiologic follow-up study," Diabetes Care. 31:1373-1379.
De Pablo, P. et al. (2009). "Periodontitis in systemic rheumatic diseases," Nat. Rev. Rheumatol. 5:218-224.
Destefano, F. et al. (1993). "Dental disease and risk of coronary heart disease and mortality," BMJ 306:688-691.
Desvarieux, M. et al. (2003). "Relationship Between Periodontal Disease, Tooth Loss, and Carotid Artery Plaque: The Oral Infections and Vascular Disease Epidemiology Study (INVEST)," Stroke 34:2120-2125.
Desvarieux, M. et al. (2005). "Periodontal Microbiota and Carotid Intima-Media Thickness," Circ. 111:576.
Doan, N. et al. (1999). "Proficiencies of three anaerobic culture systems for recovering periodontal pathogenic bacteria," J. Clin. Microbiol. 37:171-174.
Dong, Z. et al. (1998). "Intracellular Ca2+ thresholds that determine survival or death of energy-deprived cells," Am. J. Patho. 152:231-240.
Ebersole, J.L. et al. (1997). "Systemic acute-phase reactants, C-reactive protein and haptoglobin, in adult periodontitis," Clin. Exp. Immunol. 107:347-352.
El-Kamel, A.H. et al. (2008). "Oral colon targeted delivery systems for treatment of inflammatory bowel diseases: synthesis, in vitro and in vivo assessment," Int. J. Pharm. 358:248-255.
Ellen, R. et al. (1985). "*Streptococcus mutans* and Lactobacillus detection in the assessment of dental root surface caries risk," J Dent Res. 64(10):1245-1249.
Elliott, T.S.J. et al. (2004). "Guidelines for the antibiotic treatment of endocarditis in adults: report of the Working Party of the British Society for Antimicrobial Chemotherapy," J. Antimicrob. Chemother. 54:971-981.
Emori et al. Clinical Microbiology Reviews Oct. 1993, vol. 6, No. 4, pp. 428-442, "An Overview of Nosocomial Infections, Including the Role of the Microbiology Laboratory".
Emrich, L.J. et al. (1991). "Periodontal disease in non-insulin-dependent diabetes mellitus," J. Periodontol. 62:123-131.
Engelhart, M.J. et al. (2004). "Inflammatory Proteins in Plasma and the Risk of Dementia," Arch. Neurol. 61:668-672.
European Food Safety Authority (2007). "Opinion of the scientific panel on dietetic products, nutrition and allergies on a request from the commission related to the safety of α-cyclodextrin," EFSA Journal 537:1-21.
Extended European Search Report dated Nov. 4, 2016, for EP Application No. 14 775 784.3, filed on Mar. 12, 2014, 8 pages.
Ferrillo, P., Jr. et al. (2000). "Report of the ADEA president's task force on the Surgeon General's report on oral health. American Dental Education Association, "J Dent Educ. 64(10):708-714.
Fiermonte, G. et al. (1993). "Abundant bacterial expression and reconstitution of an intrinsic membrane-transport protein from bovine mitochondria," Biochem. J. 294:293-299.
Final Office Action dated Nov. 8, 2016, for U.S. Appl. No. 14/775,959, filed Sep. 14, 2015, 16 pages.
Firestein, G.S. (2003). "Evolving concepts of rheumatoid arthritis," Nature 423:356-361.
Fletcher, A.M. et al. (2010). "Incisor degeneration in rats induced by vascular endothelial growth factor/fibroblast growth factor receptor tyrosine kinase inhibition," Toxi. Patho. 38:267-279.
Fokkema, S.J. et al. (2003). "Increased release of IL-12p70 by monocytes after periodontal therapy," J. Clin. Periodontol. 30:1091-1096.

(56) References Cited

OTHER PUBLICATIONS

Forner, L. et al. (2006). "Increased plasma levels of IL-6 in bacteremic periodontis patients after scaling," J. Clin. Periodo. 33:724-729.

Gaetti-Jardim et al. Journal of Medical Microbiology 2009, vol. 58, pp. 1568-1575, "Quantitative detection of periodontopathic bacteria in atherosclerotic plaques from coronary arteries".

Gatz, M. et al. (2006). "Lifestyle risk and delaying factors," Alzheimer Dis. Assoc. Disord. 20:S84-S88.

Gerich, J.E. et al. (1984). "Abnormal glucose counterregulation in insulin-dependent diabetes mellitus," New Eng. J. Med., p. 986.

Ghezzi, P. et al. (2000). "Lps induces IL-6 in the brain and in serum largely through TNF production," Cytokine 12:1205-1210.

Gierynska, M. et al. (2002). "Induction of CD8 T-Cell-Specific Systemic and Mucosal Immunity against Herpes Simplex Virus with CpG-Peptide Complexes," J. Virol. 76:6568-6576.

Gijsenbergh, F. et al. (2005). "First human exposure of Org 25969, a novel agent to reverse the action of rocuronium bromide," Anesthesiology 103:695-703.

Gladman, D.D. (1993). "Toward unraveling the mystery of psoriatic arthritis," Arthritis Rheum. 36:881-884.

Goldschmidt, E.E. et al. (1977). "Differential counteraction of ethylene effects by gibberellin a(3) and n(6)-benzyladenine in senescing citrus peel," Plant Physiol. 59:193-195.

Grau, A.J. et al. (2004). "Periodontal Disease as a Risk Factor for Ischemic Stroke," Stroke 35:496-501.

Green, J. et al. (1985). "Protein B of soluble methane monooxygenase from *Methylococcus capsulatus* (Bath). A novel regulatory protein of enzyme activity," J. Biol. Chem. 260:15795-15801.

Griffith, H.R. et al. (2008). "Brain metabolism differs in Alzheimer disease and Parkinson disease dementia," Alzheimers Dement. 4:421-427.

Grossi, S.G. et al. (1997). "Treatment of periodontal disease in diabetics reduces glycated hemoglobin," J. Periodontol. 68:713-719.

Grubman, A. et al. (2010). "Vitamin B6 is required for full motility and virulence in Helicobacter pylori," MBio. 1:e00112-10, 9 total pages.

Gunsolley, J.C. (2006). "A meta-analysis of six-month studies of antiplaque and antigingivitis agents," J. Am. Dent. Assoc. 137:1649-1657.

Gurenlian, J.R. (2007). "The role of dental plaque biofilm in oral health," J. Dental Hygiene 81:1-11.

Hake, A.M. (2001). "Use of cholinesterase inhibitors for treatment of Alzheimer disease," Cleve. Clin. J. Med. 68:608-609, 613-614, 616.

Halawi, A.M. et al. (2013). "Chronic rhinosinusitis: epidemiology and cost," Allergy Asthma Proc. 34:328-334.

Hanberger, H. et al. (2011). "Increased mortality associated with methicillin-resistant *Staphylococcus aureus* (MRSA) infection in the intensive care unit: results from the EPIC II study," Int. J. Antimicrob. Agents 38:331-335.

Hanisah et al. Journal of Primary Health Care Mar. 2009, vol. 1, No. 1, pp. 20-25, "Prevalence of acne and its impact on the quality of life in school-aged adolescents in Malaysia".

Hansson, G.K. (2005). "ATVB in focus: Immunity and atherosclerosis," Arterio. Thromb. Vasc. Biol. 25:17.

Hautalahti, O. et al. (2007). "Failure of xylitol given three times a day for preventing acute otitis media," Pediatr. Infect. Dis. J. 26:423-427.

Hecker, M. et al. (2001). "General stress response of Bacillus subtilis and other bacteria," Adv. Microb. Physiol. 44:35-91.

Hovgaard, L. et al. (1995). "Drug delivery studies in Caco-2 monolayers. IV. Absorption enhancer effects of cyclodextrins," Pharm. Res. 12:1328-1332.

Hutchinson, Proc. Natl. Acad. Sci. USA Mar. 1999, vol. 96, pp. 3336-3338, "Microbial polyketide synthases: More and more prolific".

Ide, M. et al. (2003). "Effect of treatment of chronic periodontitis on levels of serum markers of acute-phase inflammatory and vascular responses," J. Clin. Periodontol. 30:334-340.

Indiveri, C. et al. (1992). "Identification and purification of the ornithine/citrulline carrier from rat liver mitochondria," Eur. J. Biochem. 207:449-454.

Institute of Medicine (1998). Chapter 7: Vitamin B6 in Dietary reference intakes for thiamin, riboflavin, niacin, vitamin B6, folate, vitamin B12, pantothenic acid, biotin, and choline, pp. 150-195.

International Search Report dated Jun. 10, 2014, for PCT Application No. PCT/US2014/024613, filed on Mar. 12, 2014, 3 Pages.

Ioannidis, J.P.A. et al. (2002). "Standardized retrieval of side effects data for meta-analysis of safety outcomes. A feasibility study in acute sinusitis," J. Clin. Epide. 55:619-626.

Isogai, E. et al. (1991). "Platelet aggregation induced by uncommon serotypes of *Streptococcus sanguis* isolated from patients with Behçet's disease," Arch Oral Biol. 36(6):425-429.

Itzhaki, R.F. et al. (2004). "Infiltration of the brain by pathogens causes Alzheimer's disease," Neurobiol. Aging 25:619-627.

Ivanovski, S. et al. (2001). "Expression of bone associated macromolecules by gingival and periodontal ligament fibroblasts," J Periodontal Res. 36(3):131-141.

Janket, S-J. et al. (2004). "Asymptotic Dental Score and Prevalent Coronary Heart Disease," 109:1095-1100.

Jeulin, H. et al. (2009). "Effective ribavirin concentration in mice brain using cyclodextrin as a drug carrier: evaluation in a measles encephalitis model," Antiviral Res. 81:261-266.

Jeulin, H. et al. (2008). "In vivo antiviral activity of ribavirin/α-cyclodextrin complex: evaluation on experimental measles virus encephalitis in mice," Int. J. Pharm. 357:148-153.

Joshipura, K.J. et al. (2003). "Periodontal Disease, Tooth Loss, and Incidence of Ischemic Stroke," Stroke 34:47-52.

Joshipuram, K. et al. (2004). "Periodontal disease and biomarkers related to cardiovascular disease," J Dent Res. 83(2):151-155.

Kato, S. et al. (2009). "Highly hydroxylated or γ-cyclodextrin-bicapped water-soluble derivative of fullerene: the antioxidant ability assessed by electron spin resonance method and beta-carotene bleaching assay," Bioorg. Med. Chem. Letters 19:5293-5296.

Katz, J. et al. (2000). "Characterization of Porphyromonas gingivalis-Induced Degradation of Epithelial Cell Junctional Complexes," Infect. Immun. 68:1441-1449.

Kjer-Nielsen, L. et al. (2012). "MR1 presents microbial vitamin B metabolites to MAIT cells," Nature 491:717-723 (abstract).

Kida, T. et al. (2008). "Complete removal of chlorinated aromatic compounds from oils by channel-type γ-cyclodextrin assembly," Anal. Chem. 80:317-320.

Kim et al. (2008). Cleveland CL Inic Journal of Medicine Feb. 2008, vol. 75, No. 2, pp. 89-92, "Infective endocarditis prophylaxis before dental procedures: New guidelines spark controversy".

Kim, H-Y. et al. (2011). "Oral health behaviours according to demographic characteristics in Korean adolescents: a national representative sample," Int. Dent. J. 61:168-173.

Kinane, D.F. et al. (1992). "Bioassay of interleukin 1 (IL-1) in human gingival crevicular fluid during experimental gingivitis," Arch. Oral Biol. 37:153-156.

Kinnebrew, M.A. et al. (2012). "Innate immune signaling in defense against intestinal microbes," Immunol. Rev. 245:113-131.

Kivipelto, M. et al. (2005). "Obesity and vascular risk factors at midlife and the risk of dementia and Alzheimer disease," Arch. Neurol. 62:1556-1560.

Klareskog, L. et al. (2006). "Mechanisms of disease: Genetic susceptibility and environmental triggers in the development of rheumatoid arthritis," Nat. Clin. Pract. Rheumatol. 2:425-433.

Kondo, H. et al. (1990). "In vitro action of human and porcine α-amylases on cyclomalto-oligosaccharides," Carb. Res. 204:207-213.

Kondo, K. et al. (1994). "A case-control study of Alzheimer's disease in Japan—significance of life-styles," Dementia 5(6):314-26.

Koseki, S. et al. (2012). "Alternative approach to modeling bacterial lag time, using logistic regression as a function of time, temperature, pH, and sodium chloride concentration," Appl. Environ. Microbiol. 78:6103-6112.

Kotzin, B.L. (1996). "Systemic Lupus Erythematosus," Cell 85:303-306.

(56) References Cited

OTHER PUBLICATIONS

Kozarov, E.V. et al. (2005). "Human atherosclerotic plaque contains viable invasive actinobacillus actinomycetemcomitans and porphyromonas gingivalis," pp. e17-e18.
Kubar, A. et al. (2005). "Real-time polymerase chain reaction quantification of human cytomegalovirus and Epstein-Barr virus in periodontal pockets and the adjacent gingiva of periodontitis lesions," J. Periodontal Res. 40:97-104.
Kumar C.G. et al. (1999). "Microbial alkaline proteases: from a bioindustrial viewpoint," Biotechnol. Adv. 17:561-594.
Lal, D. et al. (2009). "Antifungal treatment and chronic rhinosinusitis," Curr. Allergy Asthma Rep. 9:227-231.
Langer, R. (1990). "New methods of drug delivery," Science 249:1527-1533.
Laska, M.J. et al. (2012). "Expression of HERV-Fc1, a Human Endogenous Retrovirus, Is Increased in Patients with Active Multiple Sclerosis," J. Virol. 86:3713-3722.
Lebedeva, N.SH. et al. (2008). "Spectroscopic studies of zinc(II)tetraphenylporphyrin molecular complex with 1,4-dioxane," Spectrochim. Acta A Mol. Biomol. Spectrosc. 70:939-942.
Lee, Y.D. et al. (1992). "Effect of organic solvents on enzymatic production of cyclodextrins from unliquefied corn starch in an attrition bioreactor," Biotechnol. Bioeng. 39:977-983.
Leroy-Lechat, F. et al. (1994). "Evaluation of the cytotoxicity of cyclodextrins and hydroxypropylated derivatives," Int'l J. Pharm. 101:97-103.
Letter from John E. Nemazi (Brooks Kushman P.C.) to Emily Stein (Primal Therapies) regarding Response to Non-Final Office Action Deadline for U.S. Appl. No. 14/775,959, dated Mar. 8, 2016, 2 pages.
Lewis et al. Antimicrobial Agents and Chemotherapy Apr. 2001, vol. 45, No. 4, pp. 999-1007, "MINIREVIEW, Riddle of Biofilm Resistance".
Li, H. et al. (1996). "The relation between codon usage, base correlation and gene expression level in *Escherichia coli* and yeast," J. Theor. Biol. 181:111-124.
Liang, J. et al. (2003). "Gender differences in old age mortality: roles of health behavior and baseline health status," J. Clin. Epidemiol. 56:572-582.
Liljemark, W.F. et al. (1996). "Human oral microbial ecology and dental caries and periodontal diseases," Crit. Rev. Oral Biol. Med. 7:180-198.
Lina, B.A. et al. (2004). "Subchronic (13-week) oral toxicity study of α-cyclodextrin in dogs," Regul. Toxicol. Pharmacol. (39 Suppl.) 1:S27-S33.
Lippa, C.F. et al. (1998). "Lewy Bodies Contain Altered α-Synuclein in Brains of Many Familial Alzheimer's Disease Patients with Mutations in Presenilin and Amyloid Precursor Protein Genes," Am. J. Pathol. 153:1365-1370.
Little, C.S. et al. (2004). "Chlamydia pneumoniae induces Alzheimer-like amyloid plaques in brains of BALB/c mice," Neurobiol. Aging 25:419-429.
Loe, H. (1993). "Periodontal disease. The sixth complication of diabetes mellitus," Diabetes Care 16:329-334.
Loesche, W.J. et al. (1998). "Assessing the relationship between dental disease and coronary heart disease in elderly U.S. veterans," J. Am. Dent. Assoc. 129:301-311.
Loesche, W.J. (1986). "Role of *Streptococcus mutans* in human dental decay," Microbiol. Rev. 50:353-380.
Long, S.S. (1983). "Nasopharyngeal flora and acute otitis media," Infect. Immuno. 41:987-991.
Loos, B. (2005) "Systemic markers of inflammation in periodontitis," J Periodontol. 76(11 Suppl):2106-2115.
Machado et al. Braz Oral Res. Sep.-Oct. 2012, vol. 26, No. 5, pp. 443-449, "Detection and enumeration of periodontopathogenic bacteria in subingival biofilm of pregnant women".
Mackie, A.R. et al. (1999). "Orogenic Displacement of Protein from the Air/Water Interface by Competitive Adsorption," J. Colloid Interface Sci. 210:157-166.

Macintyre, A. et al. (2003). "Chlamydia pneumoniae infection promotes the transmigration of monocytes through human brain endothelial cells," J. Neurosci. Res. 71:740-750.
Macpherson, M. et al. (2010). Filamin and filamin-binding proteins in integrin-regulation and adhesion. Focus on: "Filamin A is required for vimentin-mediated cell adhesion and spreading," Am. J. Physiol. Cell Physiol. 298:C206-C208.
Mancini, Johns Hopkins Advanced Studies in Medicine Mar. 2008, vol. 8, No. 4, pp. 100-105, "Incidence, Prevalence, and Pathophysiology of Acne".
Mancini, A.J. et al. (2008). "The socioeconomic impact of atopic dermatitis in the United States: A systematic review," Pediatr. Dermatol. 25:1-6.
Marotta, M. et al. (2002). "Degradation of dental plaque glucans and prevention of glucan formation using commercial enzymes," Process Biochem. 38:101-108.
Marshall, J.J. et al. (1981). "Kinetic difference between hydrolyses of γ-cyclodextrin by human salivary and pancreatic α-amylases," Biochim. Biophys. Acta. 661:142-147.
Martins, L.M. et al. (2002). "Incidence of toxic Aeromonas isolated from food and human infection," FEMS Immuno. Med. Microbiol. 32:237-242.
Masada, M. et al. (1990). "Measurement of interleukin-1 alpha and -1 beta in gingival crevicular fluid: implications for the pathogenesis of periodontal disease," J Periodontal Res. 25(3):156-163.
Masaki, H. et al. (2007). "A zinc(II)-glycine complex is an effective inducer of metallothionein and removes oxidative stress," J. Dermatol. Sci. 45:73-75.
Mattila, K. et al. (1993). "Dental infections and coronary atherosclerosis," Atheroscl. 103:205-211.
Mattila, K.J. et al. (1989). "Association between dental health and acute myocardial infarction," Br. Med. J. 298:779-782.
Mattila, K. et al. (2002). "Effect of treating periodontitis on C-reactive protein levels: a pilot study," BMC Infect. Dis. 2:30, 3 total pages.
Mccullough et al. Australian Dental Journal 2008, vol. 53, pp. 302-305, "The role of alcohol in oral carcinogenesis with particular reference to alcohol-containing mouthwashes".
Mcinnes, I.B. et al. (2011). "The pathogenesis of rheumatoid arthritis," N. Engl. J. Med. 365:2205-2219.
Mclaughlin, R. et al. (1999). "Alzheimer's disease may not be a spirochetosis," Neuroreport 10:1489-1491.
Mealey, B.L. et al. (2003). "Periodontal disease and diabetes mellitus. Bidirectional relationship," Dent. Today 22:107-113.
Metzger, Z. et al. (2009). "Enhanced attachment of Porphyromonas gingivalis to human fibroblasts mediated by Fusobacterium nucleatum," J. Endod. 35:82-85.
Meurman, J.H. et al. (2007). "Probiotics: contributions to oral health," Oral Dis. 13:443-451.
Miethke et al. Microbiology and Molecular Biology Reviews Sep. 2007, vol. 71, p. 413-451, "Siderophore-Based Iron Acquisition and Pathogen Control".
Miklossy, J. (1993). "Alzheimer's disease—a spirochetosis?" Neuroreport 4:841-848.
Milgrom, P. et al. (2006). "Mutans streptococci dose response to xylitol chewing gum," J. Dent. Res. 85:177-181.
Miller, M. J., "Syntheses and therapeutic potential of hydroxamic acid based siderophores and analogs," Chemical Reviews, 89(7), 1563-1579.
Miller, L.S. et al. (1992). "The relationship between reduction in periodontal inflammation and diabetes control: a report of 9 cases," J. Periodontol. 63:843-848.
Moen, K. et al. (2005). "The long-term effect of anti TNF-alpha treatment on temporomandibular joints, oral mucosa, and salivary flow in patients with active rheumatoid arthritis: a pilot study," OralSurg. Oral Med. Oral Pathol. Oral Radiol. Endod. 100:433-440.
Moen, K. et al. (2006). "Synovial inflammation in active rheumatoid arthritis and psoriatic arthritis facilitates trapping of a variety of oral bacterial DNAs," Clin. Exp. Rheumatol. 24:656-663.
Moen, K. et al. (2003). "Immunoglobulin G and A Antibody Responses to Bacteroides forsythus and Prevotella intermedia in Sera and Synovial Fluids of Arthritis Patients," Clin. Diagn. Lab Immunol. 10:1043-1050.

(56) References Cited

OTHER PUBLICATIONS

Monasta, L. et al. (2012). "Burden of Disease Caused by Otitis Media: Systematic Review and Global Estimates," PloS One 7:e36226.

Moriishi, K. et al. (1999). "Inhibition of listeriolysin O-induced hemolysis by bovine lactoferrin," Biol. Pharma. Bull. 22:1167-1172.

Mumcu, G. et al. (2004). "Oral health is impaired in Behçet's disease and is associated with disease severity," Rheuma. 43:1028-1033.

Munro, I.C. et al. (2004). "Safety assessment of γ-cyclodextrin," Regul. Toxicol. Pharmacol. (39 Suppl.) 1:S3-S13.

Nakanishi, K. et al. (1992). "Effect of cyclodextrins on biological membrane. II. Mechanism of enhancement on the intestinal absorption of non-absorbable drug by cyclodextrins," Chem. Pharm. Bull. 40:1252-1256.

Neilands, The Journal of Biological Chemistry Issue of Nov. 10, 1995, vol. 270, No. 45, pp. 26723-26726, "Siderophores: Structure and Function of Microbial Iron Transport Compounds".

Newbrun, E. et al. (1976). "Further studies on extracellular glucans synthesized by glucosyltransferases of oral streptococci," Caries Res. 10:255-272.

Nishijo, J. et al. (2000). "Interactions of cyclodextrins with dipalmitoyl, distearoyl, and dimyristoyl phosphatidyl choline liposomes. A study by leakage of carboxyfluorescein in inner aqueous phase of unilamellar liposomes," Chem. Pharm. Bull. 48:48-52.

Nishimura, F. et al. (1998). "Periodontal disease as a complication of diabetes mellitus," Ann. Periodontol. 3:20-29.

Non-Final Office Action dated Mar. 4, 2016, for U.S. Appl. No. 14/775,959, filed Sep. 14, 2015, 18 pages.

Offenbacher, S. et al. (1996). "Periodontal infection as a possible risk factor for preterm low birth weight," J. Periodontol. 67:1103-1113.

Ohtani, Y. et al. (1989). "Differential effects of α-β-and γ-cyclodextrins on human erythrocytes," Eur. J. Biochem. 186:17-22.

Okada, Y. et al. (1988). "Some properties and the inclusion behavior of branched cyclodextrins," Chem. Pharm. Bull. 36:2176-2185.

Orhan, D.D. et al. (2010). "Antibacterial, antifungal, and antiviral activities of some flavonoids," Microbiol. Res. 165:496-504.

Pan, W. et al. (1999). "Penetration of neurotrophins and cytokines across the blood-brain/blood-spinal cord barrier," Adv. Drug Deliv. Rev. 36:291-298.

Pande, K. et al. (2013). "Passage through the mammalian gut triggers a phenotypic switch that promotes Candida albicans commensalism," Nat. Genet. 45:1088-1091.

Panizzi, P. et al. (2011). "In vivo detection of *Staphylococcus aureus* endocarditis by targeting pathogen-specific prothrombin activation," Nat. Med. 17:1142-1146.

Parry, G.J. et al. (1985). "Sensory neuropathy with low-dose pyridoxine," Neurology 35:1466-1468.

Pascual-Ramos, V. et al. (2006). "Association between dental caries and pneumonia in patients with systemic lupus erythematosus," J Rheumatol. 33(10):1996-2002.

Pereira, M.B.R. et al. (2004). "Prevalence of bacteria in children with otitis media with effusion," J. Pediatr. 80:41-48.

Peters, H.U. et al. (1989). "The influence of agitation rate on xanthan production by Xanthomonas campestris," Biotechnol. Bioeng. 34:1393-1397.

Phoenix, D.A. et al. (1993). "Phosphatidylglycerol dependent protein translocation across the *Escherichia coli* inner membrane is inhibited by the anti-cancer drug doxorubicin. Evidence for an electrostatic interaction between the signal sequence and phosphatidylglycerol," FEBS Letters 324:113-116.

Pobozsny, K. et al. (1981). "Assay of volatile oil-cyclodextrin complexes by pyrolyzis gaschromatography," Planta. Med. 42:255-259.

Potopnyk, M. et al. (2013). "An efficient synthesis of novel sucrose-containing dilactams," Monatsh Chem. 144:437-443.

Preusch, M.R. et al. (2004). "Association Between Cerebral Ischemia and Cytotoxin-Associated Gene-A-Bearing Strains of Helicobacter pylori," Stroke 35:1800-1804.

Putschky, N. et al. (2001). "Intra-articular co-infection by Borrelia burgdorferi and Chlamydia trachomatis," Ann. Rheum. Dis. 60:632-634.

Rafferty et al. Journal of Atherosclerosis Thrombosis 2011, vol. 18, pp. 72-81, "Cultivation of Enterobacter Hormaechei from Human Atherosclerotic Tissue".

Ramsey et al. PLOS Pathogens Mar. 2011, vol. 7, Issue 3, pp. 1-8, "Metabolite Cross-Feeding Enhances Virulence in a Model Polymicrobial Infection".

Raventos-Suarez, C. et al. (1982). "Plasmodium falciparum: inhibition of in vitro growth by desferrioxamine," Am. J. Trop. Med. Hyg. 31:919-922.

Raymond et al. PNAS Apr. 1, 2003, vol. 100, No. 7, pp. 3584-3588, "Enterobactin: An archetype for microbial iron transport".

Rayner, M.G. et al. (1998). "Evidence of bacterial metabolic activity in culture-negative otitis media with effusion," JAMA 279:296-299.

Rehme, M. (2010). "Saliva pH Testing: So Simple, So Potent," located at http://toothbody.com/saliva-ph-testing-so-simple-so-potent/, 3 pages.

Riviere, G.R. et al. (2002). "Molecular and immunological evidence of oral Treponema in the human brain and their association with Alzheimer's disease," Oral Microbiol. Immunol. 17:113-118.

Ryan et al. JADA Oct. 2003, vol. 134, pp. 34S-40S, "The influence of diabetes on the periodontal tissues".

Ryu et al. Biosci Biotechnol Blochem. 2000, vol. 64, No. 2, pp. 223-228, "Purification and Parial Characterization of a Novel Glucanhydrolase from Lipomyces starkeyi KSM 22 and its Use for Inhibition of Insoluble Glucan Formation".

Sanchez-Garces, M.A.S. et al. (2004). "Periimplantitis," Med. Oral Patol. Oral Cir. Bucal. 9:S63-S74.

Sansone, C. et al. (1993). "The association of mutans streptococci and non-mutans streptococci capable of acidogenesis at a low pH with dental caries on enamel and root surfaces," J Dent Res. 72(2):508-516.

Scannapieco, F.A. et al. (2003). "Associations between periodontal disease and risk for nosocomial bacterial pneumonia and chronic obstructive pulmonary disease. A systematic review," Ann. Periodontol. 8:54-69.

Scannapieco, F. (1999). "Role of oral bacteria in respiratory infection," J Periodontol. 70(7):793-802.

Schachtele et al. Infection and Immunity Aug. 1975, vol. 12, No. 2, pp. 309-317, "Dextranases from Oral Bacteria: Inhibition of Water-Insoluble Glucan Production and Ahgerence to Smooth Surfaces by *Streptococcus mutans*".

Schmidt, R. et al. (2002). "Early inflammation and dementia: a 25-year follow-up of the Honolulu-Asia Aging Study," Ann. Neurol. 52:168-174.

Scott, C.F. et al. (1993). "Purification and characterization of a potent 70-kDa thiol lysyl-proteinase (Lys-gingivain) from Porphyromonas gingivalis that cleaves kininogens and fibrinogen," J. Biol. Chem. 268:7935-7942.

Scully, C. et al. (1998). "Update On Oral Lichen Planus: Etiopathogenesis and Management," Crit. Rev. Oral Biol. Med. 9:86-122.

Senpuku, H. et al. (2003). "Systemic diseases in association with microbial species in oral biofilm from elderly requiring care," Gerontology 49:301-309.

Seth et al. PLoS One Aug. 2012, vol. 7, Issue 8, pp. 1-9, "Comparative Analysis of Single-Species and Polybacterial Wound Biofilms Using a Quantitative, In Vivo, Rabbit Ear Model".

Shi, H.N. et al. (2004). "Bacterial colonization and the development of intestinal defences," Can. J. Gastro. 18:493-500.

Shimada, A. (1982). "Adverse reactions to total-dose infusion of iron dextran," Clin. Pharm. 1:248-249.

Silvestri, T. et al. (2004). "Analysis of cartilage biomarkers in erosive and non-erosive osteoarthritis of the hands," OsteoArthritis Cartil. 12:843-845.

Sinha, B. et al. (2000). "Heterologously Expressed *Staphylococcus aureus* Fibronectin-Binding Proteins Are Sufficient for Invasion of Host Cells," Infect. Immun. 68:6871-6878.

Skiba, M.C. et al. (1994). "Functionally important residues at a subunit interface site in the RecA protein from *Escherichia coli*," J. Biol. Chem. 269:3823-3828.

(56) References Cited

OTHER PUBLICATIONS

Slade, G.D. et al. (2003). "Relationship Between Periodontal Disease and C-Reactive Protein Among Adults in the Atherosclerosis Risk in Communities Study," Arch. Intern. Med. 163:1172-1179.
Socransky, S. et al. (1992). "The bacterial etiology of destructive periodontal disease: current concepts," J Periodontol. 63(4 Suppl):322-331.
Soto-Rojas, A. et al. (1998). "Oral manifestations in patients with Sjögren's syndrome," J Rheumatol. 25(5):906-10.
Spangberg, L. et al. (1973). "Biologic effects of dental materials. 3. Toxicity and antimicrobial effect of endodontic antiseptics in vitro," Oral Surg. Oral Med. Oral Pathol. 36:856-871.
Stein, P.S. et al. (2007). "Tooth loss, dementia and neuropathology in the Nun study," J. Am. Dent. Assoc. 138:1314-1322.
Stewart, C.M. et al. (2008). "Salivary dysfunction and quality of life in Sjögren syndrome: a critical oral-systemic connection," J. Am. Dent. Assoc. 139:291-299.
Sugie, Y. et al. (2001). "CJ-15,801, a novel antibiotic from a fungus, *Seimatosporium* sp," J. Antibiot. (Tokyo) 54:1060-1065.
Suphasiriroj, W. et al. (2013). "Specificity of antimicrobial peptide LL-37 to neutralize periodontopathogenic lipopolysaccharide activity in human oral fibroblasts," J. Periodontol. 84:256-264.
Szejtli, J. et al. (2005). "Elimination of bitter, disgusting tastes of drugs and foods by cyclodextrins," Eur. J. Pharm. Biopharm. 61:115-125.
Szente, L. et al. (1998). "Spontaneous opalescence of aqueous gamma-cyclodextrin solutions: complex formation or self-aggregation?" J. Pharm. Sci. 87:778-781.
Tan, Z.S. (2005). "Bone Mineral Density and the Risk of Alzheimer Disease," Arch. Neurol. 62:107-111.
Tarrerias, A.L. et al. (2011). "The effect of inactivated Lactobacillus LB fermented culture medium on symptom severity: observational investigation in 297 patients with diarrhea-predominant irritable bowel syndrome," Dig. Dis. 29:588-591.
Taylor, B.A. et al. (2006). "Full-mouth tooth extraction lowers systemic inflammatory and thrombotic markers of cardiovascular risk," J. Dent. Res. 85:74-78.
Ten Cate, J.M. (2012). "Novel anticaries and remineralizing agents: prospects for the future," J. Dent. Res. 91:813-815.
Ten Cate, J.M. et al. (2012). "The numerous microbial species in oral biofilms: how could antibacterial therapy be effective?" Adv. Dent. Res. 24:108-111.
Thaniyavarn, S. et al. (1982). "Pyridine analogs inhibit the glucosyltransferase of *Streptococcus mutans*," Infect. Immuno. 37:1101-1111.
Tieu, D.D. et al. (2010). "Evidence for Diminished Levels of Epithelial Psoriasin and Calprotectin in Chronic Rhinosinusitis," J. Allergy Clin. Immunol. 125:667-675.
Tlaskalova-Hogenova, H. et al. (2004). "Commensal bacteria (normal microflora), mucosal immunity and chronic inflammatory and autoimmune diseases," Immunol. Letters 93:97-108.
Tombes, M.B. et al. (1993). "The effects of hydrogen peroxide rinses on the normal oral mucosa," Nurs. Res. 42:332-337.
Topcuoglu, N. et al. (2012). "Relationship between Oral Anaerobic Bacteria and Otitis Media with Effusion," Int. J. Med. Sci. 9:256-261.
Trahan, L. et al. (1996). "Emergence of multiple xylitol-resistant (fructose PTS-) mutants from human isolates of mutans streptococci during growth on dietary sugars in the presence of xylitol," J Dent Res. 75(11):1892-1900.
Uekama, K. et al. (1982). "Allevation of prochlorperazine-induced primary irritation of skin by cyclodextrin complexation," Chem. Pharm. Bull. 30:3860-3862.
Ulbrich, W. et al. (2010). "Targeted drug-delivery approaches by nanoparticulate carriers in the therapy of inflammatory diseases," J. R. Soc. Interface 7:S55-S66.
Van Crombruggen, K. et al. (2011). "Pathogenesis of chronic rhinosinusitis: inflammation," J. Allergy Clin. Immunol. 128:728-732.

Van Houte, J. et al. (1991). "Mutans streptococci and non-mutans streptococci acidogenic at low pH, and in vitro acidogenic potential of dental plaque in two different areas of the human dentition," J Dent Res. 70(12):1503-1507.
Van Houte, J. (1994). "Role of micro-organisms in caries etiology," J Dent Res. 73(3):672-681.
Van Houte, J., et al. (1994). "The predominant cultivable flora of sound and carious human root surfaces," J Dent Res. 73(11):1727-1734.
Van Ommen, B. et al. (2004). "Disposition of 14C-α-cyclodextrin in germ-free and conventional rats," Regul. Toxicol. Pharmacol. (39 Suppl.) 1:S57-S66.
Van Steenberghe, D. et al. (2001). "Effect of different mouthrinses on morning breath," J Periodontol. 72(9):1183-1191.
Vikmon, M. et al. (1985). "Solubilization of amphotericin B with γcyclodextrin," J. Antibiotics XXXVIII(12):1822-1824.
Von Arx, T. et al. (2010). "Endodontic surgery prognostic factors," J. Endod. 36:957-973.
Wagner, R.D. (2008). "Effects of microbiota on GI health: gnotobiotic research," Adv. Exp. Med. Biol. 635:41-56.
Walker, G.J. et al. (1974). "Action of α-1,6-glucan glucohydrolase on oligosaccharides derived from dextran," Carbohydr. Res. 36:53-66.
Wang, J. et al. (2011). "IgE stimulates human and mouse arterial cell apoptosis and cytokine expression and promotes atherogenesis in Apoe-/- mice," J. Clin. Invest. 121:3564-3577.
Wang, B-Y. et al. (2009). "Negative Correlation of Distributions of *Streptococcus cristatus* and Porphyromonas gingivalis in Subgingival Plaque," J. Clin. Microbiol. 47:3902-3906.
Wang Weilin, "A Study on the Siderophores of Aureobasidium pullulans," pp. 2-3 and 22, Postgraduate Dissertation, Master's Thesis of Ocean University of China; Sep. 28, 2009 (and English translation—total 9 pages).
Weaver, J.D. et al. (2002). "Interleukin-6 and risk of cognitive decline: MacArthur studies of successful aging," Neurology 59:371-378.
Welbury et al. Rheumatology 2003, vol. 42, pp. 1445-1451, "Increased prevalence of dental caries and poor oral hygiene in juvenile idiopathic arthritis".
Welch et al. American Journal of Public Health 1942, vol. 32, pp. 261-267, "Relative Toxicity of Certain Antiseptics Containing Soap and Alcohol".
Wen, Z.T. et al. (2011). "Transcriptome analysis of LuxS-deficient *Streptococcus mutans* grown in biofilms," Mol. Oral Microbiol. 26:2-18.
Whittington et al. Anesthesia 2009, vol. 64, pp. 620-624, "Bacterial contamination of stethoscopes on the intensive care unit".
WHO (2012). "Oral health," located at http://www.who.int/mediacentre/factsheets/fs318/en/, 4 pages.
WHO (2012). "World health statistics," 180 pages.
Wickens et al. Clinical & Experimental Allergy 2012, vol. 42, pp. 1071-1079, "A protective effect of Lactobacillus rhamnosus HN001 against eczema in the first 2 years of life persists to age 4 years".
WIKIPEDIA (2017). "Tooth decay," located at https://en.wikipedia.org/wiki/Tooth_decay, 18 pages.
WIKIPEDIA (2017). "Gingivitis," located at https://en.wikipedia.org/wiki/Gingivitis, 6 pages.
WIKIPEDIA (2017). "Periodontitis," located at https://en.wikipedia.org/wiki/Periodontitis, 11 pages.
WIKIPEDIA (2017). "Halitosis," located at https://en.wikipedia.org/wiki/Halitosis, 14 pages.
Wilder, R.S. (2013). "The dental hygienist research: Progress over 100 years," J. Dent. Hygiene 87:172-243.
Wollheim, F.A. (2001). "Enteropathic arthritis: how do the joints talk with the gut?" Curr. Opin. Rheumatol. 13:305-309.
Wood, R.E. et al. (1988). "Analysis of the oral manifestations of systemic sclerosis (scleroderma)," Oral Surg. Oral Med. Oral Pathol. 65:172-178.
Written Opinion of the International Searching Authority dated Jun. 10, 2014, for PCT Application No. PCT/US2014/024613, filed on Mar. 12, 2014, 5 Pages.

(56) References Cited

OTHER PUBLICATIONS

Yaffe, K. et al. (2003). "Inflammatory markers and cognition in well-functioning African-American and white elders," Neurology 61:76-80.

Yamauchi, A. et al. (2000). "Selective potassium ion recognition by benzo-15-crown-5 fluoroionophore/γ-cyclodextrin complex sensors in water," Anal. Chem. 72:5841-5846.

Yasutake, A et al. (1979). "Hydrolysis of cyclic depsidipeptides by trypsin or chymotrypsin," FEBS Letters 100:241-243.

Young, J.C. et al. (2003). "A Stress Sensor for the Bacterial Periplasm," Cell 113:1-4.

Zaborova, V.A. et al. (2011). "Species variety of *Staphylococcal microflora* of the skin in athletes engaged in water sports," Bull. Exp. Biol. Med. 151:738-740.

Zamora-Perez, A.L. et al. (2013). "Increased number of micronuclei and nuclear anomalies in buccal mucosa cells from people exposed to alcohol-containing mouthwash," Drug Chem. Toxicol. 36:255-260.

Zhou, T. et al. (2011). "Design of clinically useful macromolecular iron chelators," J. Pharm. Pharmacol. 63:893-903.

Zhang Zhenkang, ed., et al., "Modern stomatology," pp. 398-400, Science Press, vols. I & II, Jan. 2003 (and English translation—total 19 pages).

Lemos, et al., *Streptococcus mutans*: a new Gram-positive paradigm? Microbiology 159:436-445 (2013).

Seshadri, et al., "Comparison of the genome of the oral pathogen Treponema denticola with other spirochete genomes," PNAS 101(15):5646-5651.

Notice of Allowance dated Jun. 28, 2018, for U.S. Appl. No. 14/775,959, filed Sep. 14, 2015, 14 pages.

Extended European Search Report dated Mar. 14, 2022, for EP Application No. 21197637.8, filed on Mar. 12, 2014, 10 pages.

\* cited by examiner

| Subject | Time since brushing (h) | Protein (mg/dL) | Glucose (mg/dL) | Initial pH | pH 30 min post-wash |
|---|---|---|---|---|---|
| 1 | 0.5 | trace | trace | 6.75 | 7 |
| 1 | 5 | trace | trace | 7 | 7.25 |
| 1 | 7 | 30 | trace | 7.25 | 8 |
| 1 | 11 | trace | trace | 6.5 | 7.25 |
| 2 | 0.2 | 30 | trace | 6 | 7 |
| 2 | 4 | 30 | trace | 7.25 | 7.75 |
| 2 | 9 | 100 | trace | 8 | 8 |
| 2 | 11 | trace | trace | 6.5 | 7.25 |
| 3 | 4 | 100 | trace | 8.5 | 8.25 |
| 3 | 7 | 30 | trace | 7.75 | 8 |
| 3 | 13 | trace | trace | 7.25 | 8 |

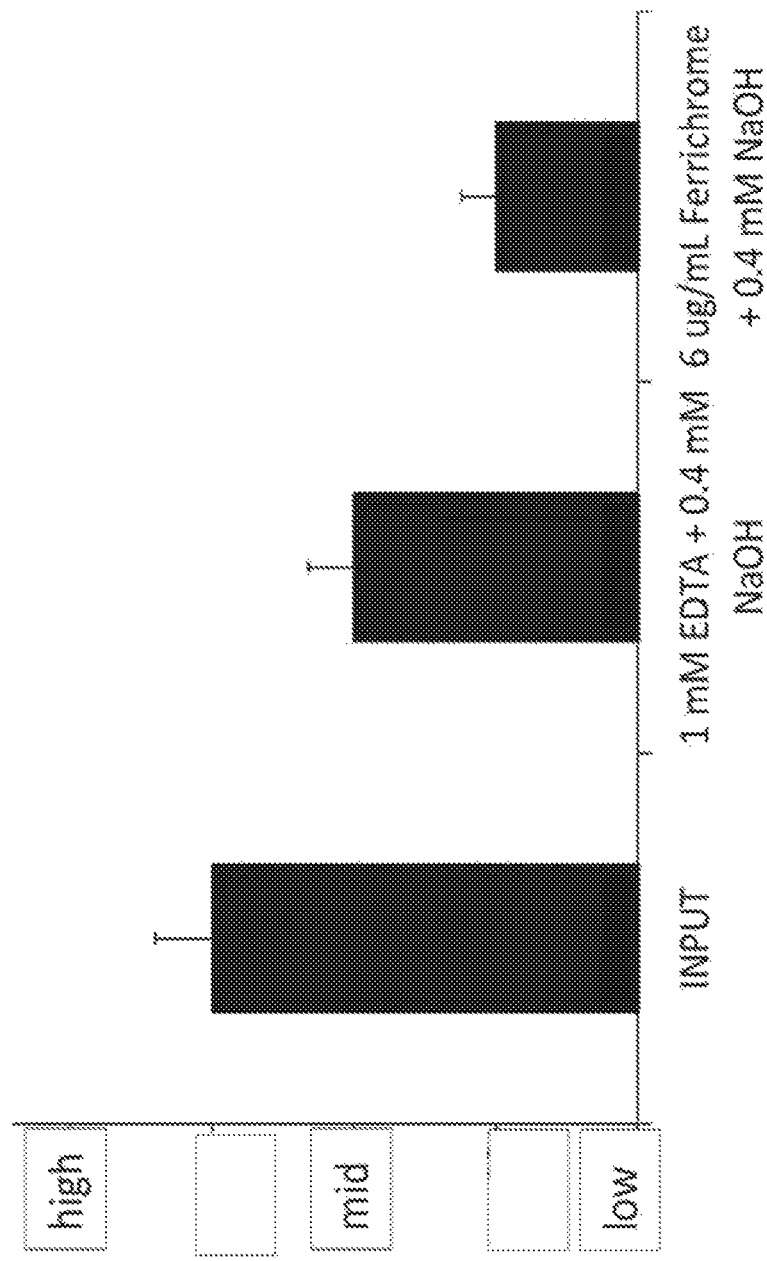

DERMAL COMPOSITION COMPRISING CHELATOR AND BASE

CROSS-REFERENCE TO RELATED APPLICATIONS

This application is a continuation of U.S. patent application Ser. No. 14/775,959, filed on Sep. 14, 2015, now U.S. Pat. No. 10,117,823, which is the U.S. National Phase of PCT Application No. PCT/US2014/024613 filed on Mar. 12, 2014, which claims priority to U.S. Provisional Patent Application No. 61/851,748, filed on Mar. 12, 2013 and U.S. Provisional Patent Application No. 61/965,678, filed on Feb. 5, 2014, the disclosures of each of which are incorporated by reference herein in their entirety.

BACKGROUND

Microbes play a central role in both mammalian health and disease, with certain microbes playing a central role in host physiology and health while other microbes promote or exacerbate disease. Health-promoting and pathogenic microbes may include bacteria, fungi, parasites and other microbes and may be found in biofilms.

Microbial biofilms are aggregates of microbial cells that adhere to each other and to a surface. The adherent cells are frequently embedded within a self-produced matrix, also referred to as an extracellular matrix generally composed of extracellular nucleic acids, proteins and polysaccharides (commonly dextran). Biofilms have been demonstrated to exist on biological or inanimate surfaces in home, agricultural, industrial and healthcare settings. A problem is often encountered with biofilms harboring pathogenic microbes and their toxic effectors that pose a health risk.

It is recognized that antibiotics have multiple limitations in their ability to inhibit the pathogenic effects of biofilms in home, agricultural, industrial and healthcare settings. Numerous attempts to neutralize the pathogenic effects of biofilms including behavioral changes, procedural changes, anti-microbial coatings and next generation antibiotics, have been made with limited success and pose significant toxicity risk to mammals. Non-toxic and effective compositions and methods of use are needed to limit the adverse effects of microbes and microbial biofilms with limited disruption of the healthy microbial flora.

Throughout this specification, various patents, patent applications and other types of publications (e.g., journal articles) are referenced. The disclosure of all patents, patent applications, and publications cited herein are hereby incorporated by reference in their entirety for all purposes.

BRIEF SUMMARY OF THE INVENTION

The invention provided herein discloses, inter alia, non-toxic compositions comprising a synergistic amount of chelator and base for limiting the adverse effects of microbes and microbial biofilms while at the same time, limiting disruption of healthy microbial flora in an individual.

Accordingly, in one aspect, provided herein are compositions comprising a chelator and a base, wherein the chelator and base provide microbial affecting activity. In some embodiments, the chelator is selected from the group consisting of siderophores, natural chelators and synthetic chelators. In another embodiment, the chelator is cyclodextrin or cyclodextrin derivative, ferrichrome, citrate, EDTA, EGTA, pectin or modified pectin. In another embodiment, more than one chelator is used. In another embodiment, the concentration of chelator is between 0.0005% and 30% of the composition. In another embodiment, the base is selected from the group consisting of natural bases, synthetic bases and agents having basic properties. In another embodiment, the base is KOH, NaOH, pyridoxal-5-phosphate, pyridoxamine, pyridoxine, vitamin K, lysine, arginine, lysozyme, alpha-galactase, tris amine or sodium bicarbonate. In another embodiment, more than one base is used. In another embodiment, the concentration of base is between 0.0001% and 15% of the composition. In another embodiment, the composition further comprises an enhancer. In another embodiment, the enhancer comprises proline, phenylalanine, boric acid, ascorbic acid or extracts from citrus, berries, teas, peppermint, mint or cinnamon. In another embodiment, the concentration of the enhancer is between 0.0001% and 10% of the composition. In another embodiment, the composition is for oral care. In another embodiment, the base comprises sodium bicarbonate and pyridoxal-5-phosphate and the chelator comprises alpha-cyclodextrin. In another embodiment, the composition is formulated in a tablet, capsule, rapid melt tablet, thin strip, gum or mouthwash. In another embodiment, the composition administered at least once per day. In another embodiment, the composition is used to promote oral health, treat or prevent cavities, periodontitis, halitosis and gingivitis. In another embodiment, the composition is used following consumption of a phosphoric acid or ascorbic acid-containing beverage. In another embodiment, the composition is used following consumption of food.

In another aspect, provided herein are methods of promoting oral health in an individual comprising: (i) identifying an individual at increased risk for developing or exhibiting signs of oral disease, (ii) measuring pH, leukocyte esterase, nitrate, microbial marker levels, or plaque-staining dye retention in the mouth of the individual, (iii) comparing said levels to healthy levels to determine if oral pathology is present, and (iv) if evidence of oral pathology is present, contacting an effective amount of a composition comprising a chelator and a base to the oral surface. In some embodiments, said method is repeated on a daily, a monthly, quarterly or annual basis. In some embodiments, said composition comprises EDTA or alpha-cyclodextrin and sodium bicarbonate or pyridoxal-5-phosphate. In some embodiments, the effective amount of EDTA and alpha-cyclodextrin is between 0.0001% and 30% of the composition. In some embodiments, the effective amount of sodium bicarbonate and pyridoxal-5-phosphate is between 0.0001% and 15% of the composition. In some embodiments, oral pathology is indicated by the individual having an oral pH below 6.2. In some embodiments, the individual is determined to have oral pathology based on the presence of one or more of the following: halitosis, tooth plaque, tooth decay, or a cavity. In some embodiments, the individual is determined to have oral pathology based on the presence of *Streptococcus mutans*.

In further aspects, provided herein are methods for limiting or eliminating microbes and/or microbial biofilms in an oral cavity of an individual comprising contacting a surface in the oral cavity with an effective amount of a composition comprising a chelator and a base. In some embodiments, said method is repeated on a daily, a monthly, quarterly or annual basis. In some embodiments, said composition comprises EDTA or alpha-cyclodextrin and sodium bicarbonate or pyridoxal-5-phosphate. In some embodiments, the effective amount of EDTA and alpha-cyclodextrin is between 0.0001% and 30% of the composition. In some embodiments, the effective amount of sodium bicarbonate and pyridoxal-5-phosphate is between 0.0001% and 15% of the composition. In some embodiments, the method further comprises assessing oral pathology in the individual, wherein oral pathology is indicated by the individual having an oral pH below 6.2. In some embodiments, the method further comprises assessing the individual for oral pathology based on the presence of one or more of: halitosis, tooth plaque, tooth decay, and/or a cavity. In some embodiments, the method further comprises assessing the individual for the presence of Streptococcus mutatis.

BRIEF DESCRIPTION OF THE DRAWINGS

FIG. 7 depicts an exemplary effect of chelator and base compositions on fungal growth.

DETAILED DESCRIPTION

Figure 1:
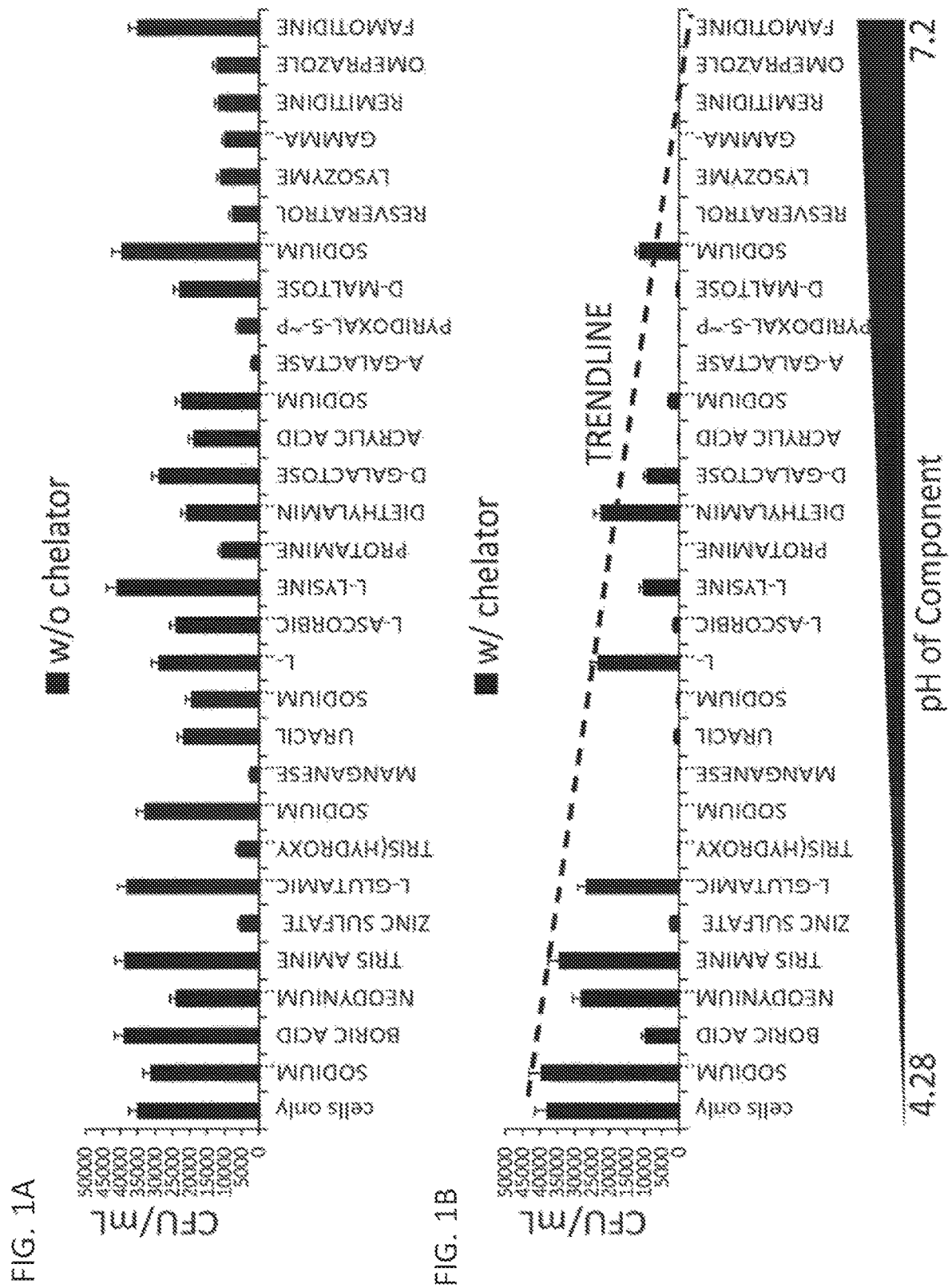
FIGS. 1A and 1B depict the effect of agents with increasing base properties+/−chelator on microbial growth.

The present invention generally relates to non-toxic compositions comprising a synergistic amount of chelator and base, whereby said base may comprise one or more hydroxyl group, pyridine ring, nitrogen group or amine group and whereby said chelator may comprise one or more ringed structure capable of chelating metal, lipid, volatile aromatic compound or microbial component. Said compositions may comprise a chelator, a base and an enhancer, whereby said enhancer enhances the utility of the chelator or base. Said compositions may be used to limit microbial growth and unwanted metabolic activity of microbes by contacting a surface to formulations comprising synergistic chelator and base compositions. Said compositions may be used to selectively inhibit the growth and viability of certain microbes while maintaining the viability of many commensal microbes of the flora. Said compositions may be used to selectively alter the metabolism of certain microbes. Said compositions may be used to prevent or treat conditions where microbes induce host inflammation. Said compositions may comprise consumable formulations or may comprise topical formulations. In certain aspects, said compositions may be administered to biological and inanimate surfaces comprising a microbial biofilm. Non-toxic compositions of the current invention may be applied frequently to a biological or inanimate surface to promote oral care, skin care, food safety, overall health and surface care. Non-toxic compositions may be used in products for oral care, skin care, food safety, overall health and surface care.

1. Definitions

As used herein, the singular form "a", "an", and "the" includes plural references unless indicated otherwise.

It is understood that aspects and embodiments of the invention described herein include "comprising," "consisting," and "consisting essentially of" aspects and embodiments.

An "individual" can be a vertebrate, a mammal, or a human. Mammals include, but are not limited to, farm animals, sport animals, pets, primates, mice and rats. Individuals also include companion animals including, but not limited to, dogs and cats. In one aspect, an individual is a human.

An "effective amount" or "therapeutically effective amount" refers to an amount of therapeutic compound, such as a composition comprising a chelator and a base, administered to an individual, either as a single dose or as part of a series of doses, which is effective to produce a desired therapeutic effect.

A "clinician" or "medical researcher" or "veterinarian" as used herein, can include, without limitation, doctors, nurses, physician assistants, lab technicians, research scientists, clerical workers employed by the same, or any person involved in determining, diagnosing, aiding in the diagnosis or influencing the course of treatment for the individual.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

II. Compositions of the Invention

Disclosed herein are non-toxic compositions, comprising chelator and base, for use in limiting microbial growth and unwanted metabolic activity and pathogenic effectors of microbes on surfaces. Said compositions may be applied to a biological or inanimate surface. Surfaces may comprise biological surfaces such as food, dermal surfaces, tooth surfaces, mucosal surfaces, gut surfaces, ocular surfaces or other and may comprise inanimate surfaces such as objects, floors, counters, utensils, handles, or other.

Also disclosed herein are non-toxic consumable compositions, comprising chelator and base, for use in limiting microbial growth, biofilm production and unwanted metabolic activity and pathogenic effectors of microbes involved in mammalian disease. Many diseases have an underlying microbial or microbial-induced inflammatory component that contributes to disease initiation or progression. Both gram-positive and gram-negative bacteria contain several components within their membranes, such as lipopolysaccharide (endotoxin), lipoteichoic acid, CpG DNA, flagella, pili, and other antigenic molecules that are potent agonists of Toll-like receptors (TLRs), which induces pro-inflammatory cytokine secretion of epithelial cells and immune cells including IL-1, IL-6, and TNF-α. Similarly, fungi and viruses may also contain antigenic molecules and TLR agonists that may trigger inflammation in a local or systemic manner, depending on the identity of the microbe, its pathogenic potential, and extent of overgrowth or metabolic activity or in cases of acute a chronic infection or intoxication.

The compositions disclosed herein may comprise one or more chelator and one or more base. Said compositions may also comprise one or more chelator and one or more base and one or more enhancer.

A. Chelator.

Chelators may comprise heterogeneous synthetic or naturally-occurring molecules capable of coordinating, and in some cases, binding cargo. Examples of cargo comprise, without limitation, metals, lipids, volatile aromatic compounds, carbohydrates, microbial components and microbes. Chelators may have more than one donor atom that may coordinate a single cargo. Chelators may also be able to coordinate more than one cargo and is dependent on chelator size and coordination groups. Chelators may be classified according to the number of donor atoms correctly positioned for potential binding to a Lewis acid or other cargo. Chelators may be bidentate, tridentate and polydentate in nature (for example, EDTA is hexadentate). Additionally, chelators may by macrocyclic whereby a large ring compound may contain several donor atoms that may bind a Lewis acid inside said ring structure. A chelator:cargo complex is called a chelate.

Examples of suitable chelators that may be used in said composition include, but are not limited to, cyclodextrins, α-cyclodextrin, β-cyclodextrin, γ-cyclodextrin, δ-cyclodextrin, methyl-β-cyclodextrin, ethylenediamine, diethylenetriamine, EDTA, EGTA, thiocyanate, porphine, heme, nitrilotriacetic acid, rhodotorulic acid, citrate, anachelins, ferrioxamines, deferoxamine mesylate, cellulose, methylcellulose, carboxymethylcellulose, citrus pectins, apple pectins, orange pectins, carrot pectins, amidated pectins, amidated low methoxyl pectin, high-ester pectins, low-ester pectins, microbial cellulosic material, agar, lignin, curcumin, chlorophylls, resveratrol, alginate, tannins, quercetin, oleuropein, HEDTA, DTPA, EDDHA, succimer, dimercaprol and derivatives thereof. Examples of chelator derivatives include but are not limited to tosylated, acylated, hydroxylalkylated, alkylated, carboxylated, methylated, hydroxypropylated, hydroxylated, sulfoalkylated, amidated, phosphorylated and sulfonated forms and the like. Said chelators may be used in free or salt form. Non-limiting examples of chelators and their use are provided in Table 1.

Suitable chelators may be used in liquid, gel, paste, créme and ointment formulations at concentrations ranging from about 500 mM to about 0.1 nM per dose, depending on the use. Some compositions may comprise chelator from about 500 mM to about 1 mM per dose. Some compositions may comprise chelator from about 500 µM to about 1 µM per dose. Other compositions may comprise chelator from about 10 µM to about 10 nM per dose. Yet other compositions may comprise chelator from about 800 nM to about 0.1 nM per dose.

Suitable chelators may be used in solid and powder formulations at amounts ranging from about 1,000 mg to about 50 ng per dose, depending on the use. Some compositions may comprise chelator from about 1,000 mg to about 50 mg per dose. Some compositions may comprise chelator from about 1 mg to about 25 µg per dose. Some compositions may comprise chelator from about 10 µg to about 100 ng per dose. Other compositions may comprise chelator from about 1 µg to about 50 ng per dose.

B. Bases

Bases may comprise an agent that donates electrons or hydroxide ions, accepts protons, may behave as Arrhenius bases, Brønsted-Lowry bases and Lewis bases. Arrhenius bases increase the hydroxyl ion concentration in a solution. Brønsted-Lowry bases accept protons. Lewis bases donate electron pairs. Bases may comprise primary, secondary, tertiary or cyclic amines.

Examples of suitable bases that may be used in said composition include, but are not limited to, pyridoxine, pyridoxal-5-phosphate, pyridoxine HCl, vitamin B6, vitamin B12, vitamin K, arginine, polyarginines, lysine, polylysines, uracil, sodium bicarbonate, analine, biogenic amines, methylamine, dimethylamine, trimethylamine, ammonia, propylamines, nitroanalines, haloamines, oximes, sodium hydroxide, potassium hydroxide and derivatives thereof. Said bases may have one or more hydroxyl group, pyridine, pyridine nitrogen group, amine or other and may comprise: vitamin base, nucleotide base, basic amino acid, basic sugar, basic lipid, basic mineral, basic salt, basic small molecule, basic peptide or basic enzyme. Said base may be used in free or salt form. Non-limiting examples of bases and their use are provided in Table 2.

Suitable bases may be used in liquid, gel, paste, créme and ointment formulations at concentrations ranging from about 250 mM to about 750 µM per dose, depending on the potency and use. Some compositions may comprise base from about 250 mM to about 1 mM per dose. Some compositions may comprise base from about 800 µM to about 5 µM per dose. Other compositions may comprise base from about 10 µM to about 100 nM per dose. Yet other compositions may comprise base from about 120 nM to about 750 µM per dose.

Suitable bases may be used in solid and powder formulations at amounts ranging from about 1,000 mg to about 50 ng per dose, depending on the potency and use. Some compositions may comprise base from about 1,000 mg to about 50 mg per dose. Some compositions may comprise base from about 75 mg to about 5 mg per dose. Some compositions may comprise base from about 5 mg to about 100 µg per dose. Other compositions may comprise base from about 0.150 µg to about 8 µg per dose. Yet other compositions may comprise base from about 7.5 µg to about 50 ng per dose.

C. Enhancers

An enhancer may comprise a synthetic or natural agent that enhances the effects of chelator or base in said composition. Enhancers may act by activating said chelator or said base; may protect or preserve said chelator or said base; may promote synergism between said chelator and said base; may act in a supplemental manner to promote synergistic effects between chelator and base to reduce the total dose of each active agent used: or other.

Examples of suitable enhancers that may be used in said composition include, but are not limited to, antacids, ion channel antagonists, proton transporter antagonists, bacteriocins, sugar hydrolyzing enzymes, neutral sugars, sugar alcohols, xylitol, mannitol, sorbitol, Stevia, antimicrobial lipids, iron-binding proteins, plant extracts and derivatives thereof. Other non-limiting examples of suitable enhancers may include extracts and oils of green tea, mint, peppermint, cinnamon, spearmint, clove, aloe, ginger, lemongrass, avocado, olive, pomegranate, acai, and citrus. Other examples of suitable enhancers may include, without limitation, binding compounds such as polyethylene glycol, polyvinyl pyrrolidone, magnesium stearate and others. Yet other examples of suitable enhancers may be, without limitation, ascorbic acid, phenylalanine, histatins, statherins, proline-rich proteins, lipase, sialoperoxidase, adhesion-modulating proteins, carbonic anhydrases, amylases, peroxidases, lactoferrin, and mucins. Said enhancers do not inhibit that activity of chelator or base in said composition.

Suitable enhancers may be used in liquid, gel, paste, creme and ointment formulations at concentrations ranging from about 100 mM to about 50 pM per dose, depending on the potency and use. In some embodiments, suitable enhancer concentrations may range from about 100 mM to about 5 mM per dose. In some embodiments, suitable enhancer concentrations may range from about 5 mM to about 50 µM per dose. In some embodiments, suitable enhancer concentrations may range from about 75 µM to about 500 nM per dose. In other embodiments, suitable enhancer concentrations may range from about 1 µM to about 10 nM per dose. Yet in other embodiments, suitable enhancer concentrations may range from about 25 nM to about 50 pM.

Suitable enhancers may be used in solid and powder formulations at amounts ranging from about 5,000 mg to about 10 ng per dose, depending on the potency and use. In some embodiments, suitable enhancer amounts may range from about 5,000 mg to about 150 mg per dose. In some embodiments, suitable enhancer amounts may range from about 200 mg to about 5 mg per dose. In some embodiments, suitable enhancer amounts may range from about 5 mg to about 250 µg per dose. In other embodiments, suitable enhancer amounts may range from about 500 µg to about 10 µg per dose. Yet in other embodiments, suitable enhancer amounts may range from about 25 µg to about 500 ng. Yet in other embodiments, suitable enhancer amounts may range from about 750 ng to about 10 ng per dose.

Chelators, bases and enhancers, or their acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as, their racemic and optically pure forms. Optically active (+) and (−), (R)- and (S)-, or (D)- and (L)-isomers may be prepared using chiral synthons or chiral reagents, or resolved using conventional techniques, such as reverse phase HPLC. When the compounds described herein contain olefinic double bonds or other centers of geometric asymmetry, and unless specified otherwise, it is intended that the compounds include both E and Z geometric isomers. Likewise, all tautomeric forms are also intended to be included.

Chelators, bases and enhancers or salts thereof may form a solvate and/or a crystal polymorph, and the present invention contains such solvates and crystal polymorphs of various types. A solvate means a solvate of the compound of the present invention or its salt, and example includes solvate of which solvent is alcohol (e.g., ethanol), hydrate, or the like. Example of hydrate includes monohydrate, dihydrate or the like. A solvate may be coordinated with an arbitrary number of solvent molecules (e.g., water molecules). The compounds or salts thereof may be left in the atmosphere to absorb moisture, and a case where adsorbed water is attached or a case where hydrate is formed may arise. Moreover, the compounds or salts thereof may be recrystallized to form their crystal polymorph.

D. Pharmaceutical Compositions

Any of the chelator and base compositions disclosed herein may be formulated into a pharmaceutical and may comprise combinations of chelator and base as the active ingredients. Pharmaceutical compositions may also comprise enhancers.

In some compositions comprising a pharmaceutically acceptable dose of chelator or base or comprising a pharmaceutically acceptable chelator or base may require FDA approval as a pharmaceutical for use to treat a microbe-mediated inflammatory disease.

Pharmaceutical compositions may be formulated with appropriate pharmaceutically acceptable excipients, carriers, diluents or vehicles, and may be formulated into preparations in solid, semi-solid, liquid, gels, pastes, suspension, emulsion, or gaseous forms, and may be formulated into a pharmaceutically acceptable dosage form such as: tablets, capsules, caplets, gums, powders, granules, ointments, crèmes, solutions, suspensions, emulsions, suppositories, injections, inhalants, gels, nanoparticles, microspheres, and aerosols. As such, administration may be achieved in various ways, usually by oral or topical administration. In pharmaceutical dosage forms, the chelator and base may be administered in the free form or in the form of their pharmaceutically acceptable salts, or they may also be used in a time-release formulation, or they may be administered sequentially in a discrete manner, or they may also be used in combination with other pharmaceutically active compounds.

The term "pharmaceutical dose" or "pharmaceutical dosage form," refers to physically discrete units suitable as unitary dosages for humans and other mammals, each unit comprising a predetermined quantity of agents in an amount calculated sufficient to produce the desired effect in association with an acceptable diluent, carrier, or vehicle of a formulation. The specifications for the unit dosage forms may depend on the particular chelator and base combination employed, the effect to be achieved, the route of administration and the pharmacodynamics associated with the mammal.

For demonstrating the synergistic activity of the selected chelator and base agents to be used in a pharmaceutical composition and for establishing an appropriate fixed-dose ratio for efficacy against microbe-mediated or microbe-enhanced inflammatory diseases, varying amounts of the two agents are administered to appropriate animal models of inflammatory disease, either at a time of active disease (following disease onset) or at an early time point representative of pre-clinical disease, and the effect on disease activity or progression is measured. Alternatively, the effects of varying amounts of the two agents may be tested on a cellular response mediating inflammation that may be involved in the pathogenesis of said disease. Alternatively, the effects of varying amounts of the two agents in various formulations may be tested on a microbial response; the presence, absence or degree of pathogenic effectors; metabolic processes and/or growth that may be involved in the pathogenesis of said disease as a means to determine the appropriate dose and ratio for use as a pharmaceutical composition.

In some pharmaceutical compositions, suitable chelators may comprise cyclodextrins, pectins, modified pectins, ethylenediamine, diethylenetriamine, EDTA, EGTA, thiocyanate, porphine, heme, nitrilotriacetic acid, rhodotorulic acid, citrate, anachelins, ferrioxamines, deferoxamine mesylate, their salts, derivatives or other.

In some pharmaceutical compositions, suitable bases may comprise analines, biogenic amines, methylamine, dimethylamine, trimethylamine, pyridoxine, pyridoxal-5-phosphate, pyridoxamine, ammonia, sodium bicarbonate, ammonium salts, propylamines, nitroanalines, haloamines, oximes, sodium hydroxide, potassium hydroxide or other. For oral formulations, the agents may be used alone or in combination with appropriate additives to make tablets, powders, granules, gums, lozenges, rapid melt tablets, capsules, gels, pastes, solutions or suspensions. Said formulations may further comprise conventional additives, such as xylitol, mannitol, sorbitol, stevia or the like; with binders, such as crystalline cellulose, cellulose derivatives, acacia, starches, gelatins or the like; with disintegrators, such as starches, carboxymethylcellulose or the like; with lubricants, such as talc, magnesium stearate or the like; and if desired, with diluents, buffering agents, moistening agents, preservatives, and flavoring agents.

Acceptable excipients, such as vehicles, adjuvants, carriers or diluents, are commercially available. Moreover, acceptable auxiliary substances, such as pH-adjusting and buffering agents, tonicity-adjusting agents, stabilizers, wetting agents and the like are commercially available. Any compound useful in the methods and compositions of the invention can be provided as an acceptable base-addition salt. "Acceptable base-addition salt" refers to those salts that retain the biological effectiveness and properties of the free acids, which are not biologically or otherwise undesirable. These salts are prepared by adding an inorganic base or an organic base to the free acid. Salts derived from inorganic bases include, but are not limited to, the fluoride, sodium, potassium, lithium, ammonium, calcium, magnesium, iron, zinc, copper, manganese, aluminum salts and the like. Preferred inorganic salts are the ammonium, fluoride, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Exemplary organic bases are isopropylamine, diethylamine, ethanolamine, trimethylamine, dicyclohexylamine, choline, and the like.

E. Nutritional Supplement Compositions

Any of the chelator and base compositions disclosed herein may be Generally Recognized as Safe (GRAS) and may be used in amounts at or below the FDA recommended daily allowance. Said compositions may be used as a nutritional supplement to promote health. In some embodiments, compositions may be used to promote health in a localized manner and may be dependent on the route of administration, dose or absorption kinetics and dynamics.

Said compositions may be formulated with acceptable carriers or diluents, and may be formulated into preparations in solid, semi-solid, pressed powder, powder, liquid, gel, suspension, emulsion, or gaseous forms, and may be formulated into preparations such as liquids, syrups, concentrates, tablets, capsules, caplets, powders, rapid melts, thin strips, granules, ointments, cremes, solutions, suspensions, emulsions, suppositories, injections, inhalants, gels, microspheres, nanoparticles, crystals and aerosols. As such, dose administration may be achieved in various ways, usually by oral administration. In nutritional supplement dosage forms, the chelator and base may be administered in the form of their acceptable salts, or they may also be used in a time-release formulation, or they may be used in combination with other nutritional supplement compounds.

Nutritional supplement compositions may comprise suitable chelators such as: cyclodextrins such as α-cyclodextrin, β-cyclodextrin, γ-cyclodextrin, δ-cyclodextrin, methyl-β-cyclodextrin, and their derivatives; celluloses such as methylcellulose, carboxymethylcellulose, cellulosic material from algae and lignin and their derivatives; pectins from citrus, apple, orange, carrot or other, modified pectins such as amidated pectins, amidated low methoxyl pectins, high-ester pectins, low-ester pectins and other; and various other chelators such as agar, curcumin. chlorophylls, resveratrol, alginate, tannins, quercetin, oleuropein, EDTA and EGTA.

Nutritional supplement compositions may comprise suitable bases such as: vitamin bases such as pyridoxine, pyridoxamine, pyrodoxal-5-phosphate, pyridoxine HCl, vitamin B6, vitamin B12, vitamin K; basic amino acids and derivatives such as arginine, polyarginines, lysine, polylysines, protamine sulfate; uracil; basic salts such as sodium bicarbonate and others: sodium hydroxide and potassium hydroxide.

For oral formulations, the agents may be used alone or in combination with appropriate additives to make tablets, powders, pressed powders, crystals, granules, capsules, gums, lozenges, rapid melt tablets, capsules, gels, thin strips, pastes, solutions or suspensions. Said formulations may further comprise conventional additives, such as xylitol, mannitol, sorbitol, stevia or the like; with binders, such as crystalline cellulose, cellulose derivatives, acacia, starches, gelatins or the like; with disintegrators, such as starches, carboxymethylcellulose or the like; with lubricants, such as talc, magnesium stearate or the like: and if desired, with diluents, buffering agents, moistening agents, preservatives, and flavoring agents.

The agents may be encapsulated in gelatin capsules together with inactive ingredients and powdered carriers, such as, but not limited to, glucose, lactose, sucrose, sucralose, mannose, mannitol, xylitol, stevia, aspartame, neotame, acesulfame potassium, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features include, without limitation, red iron oxide, silica gel, sodium lauryl sulfate, titanium dioxide, and edible white ink. Similar diluents may be used to make compressed tablets. Both tablets and capsules may be manufactured as sustained release products to provide for continuous release of agents over a period of minutes. Compressed tablets may be sugar coated or film coated to mask any unpleasant taste and protect the tablet from the atmosphere, or enteric-coated for selective disintegration in the gastrointestinal tract. Liquid dosage forms for oral administration may contain coloring and flavoring to increase aesthetic experience Compressed tablets may be generated using a process known as wet granulation, whereby the active agents may be mixed in powder form with inactive ingredients. Once mixed, the powder may be forced through a mesh screen in a process called dry screening. The mixture may then molded into a tablet using mechanical compression by a punch and die system. The final tablet may then be coated for aesthetics. Compressed tablets may also be generated using a process using a tablet press, whereby the active agents may be mixed in dry powder form with inactive ingredients. Once mixed, the dry powder may be molded into a tablet using mechanical compression by a punch and die system.

For oral administration of dietary supplement compositions to the mucosal surfaces of the mouth, throat and upper digestive tract, the active agents with other suitable agents may be made into formulations such as liquids, fast melting capsules, fast-dissolving tablets, powders, gels, thin strips and lozenges. In one embodiment, a composition may be formulated into a fast-dissolving thin strip and may comprise dehydrated polymer to act as an excipient, such as cellulose, gelatin or starch that, when hydrated under the tongue with saliva may dissolve to release the chelator and base. In another embodiment, a composition may be formulated into a fast-dissolving lozenge and may comprise liquid paraffin, sugar-substitutes, sugar alcohols, non-crystallizing sorbitol solution, flavoring agent, coloring agent or the like, and may release the chelator and base to the tongue, throat and esophagus. In another embodiment, a composition may be formulated into a fast-dissolving tablet and may comprise disintegrant, filler, sugar alcohol, flavoring agent, coloring agent or the like, and may release the chelator and base to the tongue, teeth, gums and mucosal surfaces of the mouth. In another embodiment, a composition may be formulated into a gel and may comprise cellulose, gelatin, pectin or other polymer, sugar alcohols, flavoring agent, coloring agent or the like and may release the chelator and base to the surfaces of the mouth, teeth, tongue, throat, and esophagus.

Acceptable excipients, such as vehicles, adjuvants, carriers or diluents, are commercially available. Moreover, acceptable auxiliary substances, such as pH-adjusting and buffering agents, tonicity-adjusting agents, stabilizers, wetting agents and the like are commercially available. Any compound useful in the methods and compositions of the invention can be provided as an acceptable base-addition salt. "Acceptable base-addition salt" refers to those salts that retain the biological effectiveness and properties of the free, acids, which are not biologically or otherwise undesirable. These salts are prepared by adding an inorganic base or an organic base to the free acid. Salts derived from inorganic bases include, but are not limited to, the fluoride, sodium, potassium, lithium, ammonium, calcium, magnesium, iron, zinc, copper, manganese, aluminum salts and the like. Preferred inorganic salts are the ammonium, fluoride, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Exemplary organic bases are isopropylamine, diethylamine, ethanolamine, trimethylamine, dicyclohexylamine, choline, and caffeine.

F. Food Safety, Cosmetic, and Surface-Cleaning Compositions

Any of the chelator and base compositions disclosed herein may be GRAS agents and may be used as food additives to promote health. Food additive compositions may be formulated may be formulated as food sprays, food washes or concentrates. Food safety formulations may be used to promote health or to limit undesired microbial metabolism and thus may serve as food safety agents, food preparatory agents and/or food preservatives.

Some food safety compositions may be used directly on food surfaces or may be used as preservative in food products. Said compositions may comprise EDTA, sodium pyrophosphate and gamma-cyclodextrin as chelator; and pyridoxal-5-phosphate, NaOH, lysine and sodium pyrophosphate as base. Compositions may comprise chelator concentration at about 0.1 mM to about 0.1 µM and base concentration at about 0.1 mM to about 0.1 µM.

Additionally, food safety formulations may be applied frequently or on an as needed basis to surfaces or objects such as: cutting board, kitchen counter, kitchen sink, food-processing devices such as conveyer belts, knives, forks, hooks, gloves or other and food storage devices such as packaging, containers, boxes or other.

In some embodiments, food safety compositions may comprise EDTA, EGTA, rhodotorulic acid and ferrichrome as chelator; protamine sulfate, tris amine, tris(hydroxymethyl)aminomethane hydrochloride, diethylamine hydrochloride, KOH and NaOH as base; and boric acid, and sodium orthovanadate as enhancer. In some surface care compositions acceptable chelator concentrations may range from about 100 mM to about 1 µM, acceptable base concentrations may range from about 500 µM to about 1 µM and acceptable enhancer concentrations may range from about 50 µM to about 10 nM.

In other food safety compositions for use on food preparation surfaces and food storage surfaces may comprise ferrichrome, EDTA and rhodotorulic acid as chelator; KOH, NaOH and sodium bicarbonate as base and sorbic acid as enhancer. In said compositions, EDTA may be used at concentrations of ranging from about 0.1 M to about 0.1 mM, rhodotorulic acid may be used at concentrations of about 10 µM to about 10 nM, ferrichrome may be used at concentrations of about 5 mM to 5 µM; KOH and NaOH may be used at concentrations of about 0.8 M-0.5 µM; sodium bicarbonate may be used at about 0.1 M to about 0.1 mM; sorbic acid may be used at concentrations of about 0.5 mM to about 0.5 µM.

Any of the chelator and base compositions disclosed herein may be GRAS agents and may be suitable for formulation in a cosmetic to limit undesired microbial growth, undesired microbial metabolism and thus serve as a preservative and/or a deodorant. Cosmetic compositions may be formulated in an elution patch, wipe, pad, sponge, cloth, strip, gel, paste, solution, emollient, serum, moisturizer, make-up, lotion, shampoo, conditioner, gel, mousse, soap, deodorant, antiperspirant, spray, wash and solution and may be used for topical administration.

In some compositions, acceptable chelator and base may be used for veterinary applications such as in formulations for promoting oral health, wound care or other. Veterinary formulations may include sprays, gels, liquids, syrups, tablets, capsules, lotions, salves, or other.

Any of the chelator and base compositions disclosed herein may be used as surface cleaners, disinfectants, or other. Surface treatments may be formulated as concentrates, solutions, sprays, powders, wipes or other. Surfaces may include: biologic surfaces comprising oral, gut, nasal, ocular, otic, topical, food or other, inanimate surfaces comprising structural surfaces, clothing, gloves, diapers, undergarments, kitchen surfaces, bathroom surfaces, painted surfaces, tiled surfaces, door knobs, handles, computers, remote controls, steering wheels, cell phones, manufacturing machinery, hospital surfaces, devices or other.

G. Health-Promoting Compositions

Associations between chronic oral infections and oral inflammation and rheumatologic disease, autoimmune diseases neurodegenerative diseases, respiratory diseases, cardiovascular diseases and stroke, and low-birth-weight/premature births are being realized (U.S. Surgeon General, WHO). Microbe-mediated and microbe-enhanced inflammatory diseases may include autoimmune diseases including rheumatoid arthritis, Crohn's disease, psoriasis, psoriatic arthritis, systemic lupus erythematosus, oral lichen planus, Behçet's disease, Sjogren's syndrome and other autoimmune diseases; degenerative diseases including osteoarthritis, stroke, cardiovascular disease, atherosclerosis, Alzheimer's disease, other dementias, macular degeneration, chronic obstructive pulmonary disease, halitosis, irritable bowel disease and other degenerative diseases; chronic infections including human immunodeficiency virus infection, hepatitis C virus infection, cytomegalovirus infection, otitis media, periodontal disease, cavities, sinusitis, rhinitis, pneumonia, rheumatic fever, endocarditis, pericarditis, and other viral, bacterial, fungal, parasite and other infection. Accordingly, any of the chelator and base compositions disclosed herein may be used to promote one or more of oral health, cardiovascular health, mental health, and/or systemic health.

Oral Health.

Oral health relates to the balance of beneficial and pathogenic activities in the oral and nasopharyngeal cavities and is critically dependent on the relationship between the microbial flora and mucosal immunity. Diseases such as, but not limited to, cavities (CV), gingivitis (CV), periodontal disease (PD), rheumatic fever (RF), otitis media (OM), sinus infection (SI), chronic rhinosinusitis (CRS), chronic halitosis (HIT) and pneumonia (PN) may stem from oral imbalance, oral microbial overgrowth, microbial effectors, undesirable microbial metabolic products and/or inflammation.

Cardiovascular Health.

Cardiovascular health relates to the balance of beneficial and pathogenic activities in the cardio-pulmonary-vascular system. Build-up of inflammatory plaques and/or chronic infections of the heart, cardio-pulmonary and/or vasculature may arise from microbial biofilm formation, microbial infection, microbial effectors, undesirable microbial metabolic products and/or inflammation. Non-limiting examples of cardiovascular diseases with microbial and microbial-related inflammation may include: Rheumatic fever (RF), atherosclerosis (AS), stroke (ST), cardiovascular disease (CVD) and chronic obstructive pulmonary disease (COPD).

Mental Health.

Mental health relates to the balance between beneficial and pathogenic activities of the brain and central nervous system and may be directly or indirectly impacted by build-up of inflammatory plaques and/or chronic infections of the brain and central nervous system and may arise from microbial biofilm formation, microbial infection, microbial effectors, undesirable microbial metabolic products and/or inflammation. Non-limiting examples of mental health conditions comprise Alzheimer's disease (AD), dementias (DM), depression, Parkinson's disease, amyotrophic lateral sclerosis and others.

Systemic Health.

Systemic health relates to the balance of beneficial and pathogenic activities of organs, organ systems and tissues of the body and may be directly or indirectly impacted by build-up of microbial overgrowth, inflammatory plaques and/or chronic infections in the body. Non-limiting examples of systemic health conditions comprise Behcet's Disease (BD), Sjogren's Syndrome (SS), lichen planus (LP), systemic lupus erythematosus (SLE), Rheumatoid arthritis (RA), and other autoimmune diseases having disease manifestations involving microbes or microbe-mediated inflammation; degenerative diseases such as irritable bowel disease (IBD), colitis (CO), osteoarthritis (OA), diabetes, metabolic diseases and cancers.

Examples of chelator and base compositions for use in promoting health may comprise one or more chelator, base and enhancer. Compositions may comprise EGTA, EDTA, citrate, cyclodextrins, vitamin B12, pectins and deferoxamine mesylate as chelator: KOH, NaOH, lysine, arginine, sodium bicarbonate, a-galactase, pyridoxal-5-phosphate, pyridoxine, pyridoxamine, vitamin B6, lysozyme and vitamin K as base; and ascorbic acid, proline, uracil, remitidine, famotidine, omeprazole and other acid blockers, plant extracts and zinc chloride as enhancer. Commercially available flavoring agents, coloring agents, fillers, excipients, carriers, and buffers may be formulated into health-promoting compositions.

III. Methods of the Invention

A. Methods for Promoting Oral Health

Any of the chelator and base compositions (e.g., pharmaceutical compositions) disclosed herein can be used in methods to promote oral health. Many microbial metabolic products have beneficial effects for mammals (examples are fermented foods and beverages). Many other microbial metabolic products have pathogenic effects on mammals (Ramsey et al. (2011) *PLOS Pathogens*). In some embodiments, administration of compositions comprising chelator and base can affect microbial metabolism, namely acid production. Non-limiting examples of oral pathologies capable of treatment by the methods disclosed herein employing any of the compositions disclosed herein include cavities (CV), gingivitis (GV), periodontal disease (PD), rheumatic fever (RF), otitis media (OM), sinus infection (SI), chronic rhinosinusitis (CRS), chronic halitosis (HT) or pneumonia (PN).

In some aspects, said method can comprise: (i) identifying an individual at increased risk for developing or exhibiting signs of oral disease, (ii) measuring pH, leukocyte esterase, nitrate, microbial marker levels, or plaque-staining dye retention in the mouth of the individual, (iii) comparing said levels to healthy levels to determine if oral pathology is present, and (iv) if evidence of oral pathology is present, contacting an effective amount of a composition comprising a chelator and a base to the oral surface.

In another aspect, any of the chelator and base compositions (e.g., pharmaceutical compositions) disclosed herein may be used in methods for limiting or eliminating microbes and/or microbial biofilms in an oral cavity of an individual comprising contacting a surface in the oral cavity with an effective amount of any of the compositions disclosed herein.

B. Methods for Promoting Cardiovascular Health

Any of the chelator and base compositions (e.g., pharmaceutical compositions) disclosed herein can be used in methods to promote cardiovascular health. Non-limiting examples of cardiovascular pathologies capable of treatment by the methods disclosed herein employing any of the compositions disclosed herein include Rheumatic fever (RF), atherosclerosis (AS), stroke (ST), cardiovascular disease (CVD) and chronic obstructive pulmonary disease (COPD). In some aspects, said method can comprise: (i) identifying an individual at increased risk for developing or exhibiting signs of a cardiovascular disease and (ii) administering a clinically effective amount of any of the compositions disclosed herein to the individual. In other aspects, said method comprises administering a clinically effective amount of any of the compositions disclosed herein to an individual diagnosed with or thought to be afflicted with a cardiovascular disease.

C. Methods for Promoting Menial Health

Any of the chelator and base compositions (e.g., pharmaceutical compositions) disclosed herein can be used in methods to promote mental health. Non-limiting examples of mental or neurological pathologies capable of treatment by the methods disclosed herein employing any of the compositions disclosed herein include Alzheimer's disease (AD), dementias (DM), depression, Parkinson's disease, and amyotrophic lateral sclerosis. In some aspects, said method can comprise: (i) identifying an individual at increased risk for developing or exhibiting signs of a mental disease and (ii) administering a clinically effective amount of any of the compositions disclosed herein to the individual. In other aspects, said method comprises administering a clinically effective amount of any of the compositions disclosed herein to an individual diagnosed with or thought to be afflicted with a mental or neurological disease.

D. Methods for Promoting Metal Health

Any of the chelator and base compositions (e.g., pharmaceutical compositions) disclosed herein can be used in methods to promote systemic health. Non-limiting examples of systemic pathologies capable of treatment by the methods disclosed herein employing any of the compositions disclosed herein include Behcet's Disease (BD), Sjogren's Syndrome (SS), lichen planus (LP), systemic lupus erythematosus (SLE), Rheumatoid arthritis (RA), and other autoimmune diseases having disease manifestations involving microbes or microbe-mediated inflammation; degenerative diseases such as irritable bowel disease (IBD), colitis (CO), osteoarthritis (OA), diabetes, metabolic diseases and cancers. In some aspects, said method can comprise: (i) identifying an individual at increased risk for developing or exhibiting signs of a systemic disease and (ii) administering a clinically effective amount of any of the compositions disclosed herein to the individual. In other aspects, said method comprises administering a clinically effective amount of any of the compositions disclosed herein to an individual diagnosed with or thought to be afflicted with a systemic disease (such as, but not limited to an autoimmune disease or an inflammatory disease).

E. Administration

Any of the chelator and base compositions (e.g., pharmaceutical compositions) disclosed herein may be administered on a frequent basis to affect microbial growth, microbial metabolism, microbial biofilm integrity, microbial biofilm production, microbial toxin production or microbial acid production. Said compositions may be administered on a frequent basis to affect microbial effectors and thus reduce inflammation. Said compositions may be administered on a frequent basis for the promotion and maintenance of health.

It is within the level of skill of a clinician or medical researcher or veterinarian to determine the preferred route of administration and the corresponding dosage form and amount, as well as the dosing regimen, i.e., the frequency of dosing. In some embodiments, the composition may be delivered in multi-dosing format whereby said composition may be administered several times a week, once a day, twice a day, three times a day, or more to achieve the appropriate therapeutic level. However, this generalization does not take into account such important variables as the specific type of microbial species to be affected, the specific inflammatory disease, the specific therapeutic agent involved and its pharmacokinetic profile, and the specific individual involved. For other approved products in the marketplace, much of this information is already provided by the results of clinical studies carried out to obtain such approval. In other cases, such information may be obtained in a straightforward manner in accordance with the teachings and guidelines contained in the instant specification taken in light of the knowledge and skill of the artisan. The results that are obtained may also be correlated with data from corresponding evaluations of past and current marketed product(s) utilizing comparable clinical testing methods.

Frequency of administration may be once a month, once a week, once a day, up to 3 times per day, up to 10 times a day, before bed and on an as-needed basis. Frequency of administration may be dependent on the identity and concentration of the base and chelator in said composition- and may be dependent on disease risk assessment, disease severity, test results, or personal preference; and may be dependent on formulation.

Individuals and other mammal at increased risk for development of a microbe-mediated or microbe-enhanced inflammatory disease, with early-stage of disease, or with established disease may be treated with a clinically effective amount of any of the compositions disclosed herein to prevent the development of disease, to prevent the progression of disease, and to prevent the progression of the symptoms or signs of disease. The total of a dose of base may generally range from about 0.00003 to about 5 mg/dose and the total of a multi-day dose may range between about 0.0003 to about 25 mg/day. The total of a dose of chelator may generally range from about 0.0005 to about 10 mg/dose and the total of a multi-day dose may range between about 0.003 to about 30 mg/day. The total dose of enhancer may vary and may generally range from about 0.00001 to 15 mg/dose.

In some embodiments, an individual may be administered any of the health-promoting compositions disclosed herein, wherein said compositions can comprise a chelator agent of at least about 0.003 mg, at least about 0.006 mg, at least about 0.01 mg, at least about 0.03 mg, at least about 0.06 mg, at least about 0.1 mg, at least about 0.125 mg, at least about 0.25 mg, at least about 0.5 mg at least about 0.75 mg, at least about 1.0 mg, at least about 3.0 mg, at least about 5.0 mg, at least about 10.0 mg, at least about 25 mg, at least about 50 mg, not more than about 5.0 g; and base agent in a single dose of at least 0.0003 mg, at least about 0.0006 mg, at least about 0.001 mg, at least about 0.003 mg, at least about 0.006 mg, at least about 0.01 mg, at least about 0.03 mg, at least about 0.06 mg, at least about 0.1 mg, at least about 0.3 mg, at least about 0.6 mg, not more than about 30.0 mg.

In some embodiments, an individual may be administered any of the health-promoting compositions disclosed herein, wherein said compositions can comprise cyclodextrin or a cyclodextrin derivative in a single dose of at least about 0.003 mg, at least about 0.006 mg, at least about 0.01 mg, at least about 0.03 mg, at least about 0.06 mg, at least about 0.1 mg, at least about 0.125 mg, at least about 0.25 mg, at least about 0.5 mg, at least about 0.75 mg, at least about 1.0 mg, at least about 3.0 mg, at least about 5.0 mg, at least about 10.0 mg, at least about 25 mg, at least about 50 mg, not more than about 5.0 g; and vitamin B6, pyridoxal-5-phosphate, pyridoxamine, pyridoxine or another vitamin base in a single dose of at least 0.0003 mg, at least about 0.0006 mg, at least about 0.001 mg, at least about 0.003 mg, at least about 0.006 mg, at least about 0.01 mg, at least about 0.03 mg, at least about 0.06 mg, at least about 0.1 mg, at least about 0.3 mg, at least about 0.6 mg, not more than about 30.0 mg; and sodium bicarbonate or other basic salt in a single dose of at least 0.0003 mg, at least about 0.0006 mg, at least about 0.001 mg, at least about 0.003 mg, at least about 0.01 mg, at least about 0.03 mg, at least about 0.06 mg, at least about 1.0 mg, at least about 5.0 mg, at least about 25 mg, at least about 50 mg, at least about 100 mg, at least about 250 mg, at least about 800 mg, at least about 1000 mg, at least about 2000 mg, not more than about 8.0 g.

Any of the chelator and base compositions (e.g., pharmaceutical compositions) disclosed herein may be administered in a manner to deliver base and chelator agents in combination or in sequence. In some embodiments, health-promoting compositions may be administered in a periodic manner. Administration of compositions may occur at least once daily, weekly or monthly or on an as needed basis. Health-promoting compositions may comprise pharmaceutically acceptable formulations (such as carriers or excipients) or may be nutritional supplement formulations. Health-promoting compositions may be commercialized in individual dose forms or in multi-dosing forms.

Methods of use for food safety formulation comprise of contacting the composition to a surface prior to, periodically during and/or immediately following the preparation of food and food products. Preferred methods involve contacting said surface with said compositions for a minimum of 5 seconds. Preferred methods also involve the periodic rinsing of contacted surfaces to effectively remove the neutralized microbes, biofilms and metabolic products.

F. Methods for Selecting Base and Chelator Compositions

Methods of selecting base and chelator compositions depend on use. Compositions may be determined by ranking base, chelator and enhancer agents, from most desired to least desired, for multiple parameters such as safety, solubility, compatibility, pH, potency, taste, consistency, smell and others. Examples of ranking base and chelator agents for determining selection in a composition for a desired use are presented in Tables 1 and 2.

Non-toxic chelator and base compositions may be ranked according to the desired parameters of potency and approved-for-oral-consumption. A desired parameter such as potency for a candidate chelator or base may be given a score of "1" for most desired and a score of "3" for least desired. In one embodiment, candidate chelators, bases and enhancers may be ranked by FDA approval for oral consumption. Agents with a score of "1" may have approval for the desired indication and a score of "3" may not have approval or may not be approved for the desired indication. The resultant overall score may be tabulated and may be used to facilitate selection. In this example, the lowest overall score represents the best candidates for use in a non-toxic composition.

TABLE 1

CHELATORS THAT MAY BE USED IN COMBINATION WITH BASE AGENTS

| CHELATOR | POTENCY^ | CONSUMABLE | ANTICIPATED USE* |
|---|---|---|---|
| Resveratrol | 2 | 1 | O, T, V, F, S |
| Quercetin | 1 | 1 | O, T, V, F, S |
| Curcumin | 2 | 1 | O, T, V, F, S |
| Oleuropein | 2 | 1 | O, T, V, F, S |
| Inositol hexaphosphate | 2 | 1 | O, T, V, F, S |
| EGCG | 1 | 1 | O, T, V, F, S |
| Amidated Pectins | 1 | 1 | O, T, V, F, S |
| Alginate | 1 | 1 | O, T, V, F, S |
| Tannic acid | 1 | 1 | O, T, V, F, |
| Chitosan | 2 | 2 | O, T, V, F, S |
| Exopolysaccharide | 1 | 2 | F, S |
| Cellulosic material | 1 | 2 | O, T, V, F, S |
| Pectins | 1 | 1 | O, T, V, F, S |
| Citrate, Citrate salts | 3 | 1 | O, T, V, F, S |
| Anachelins | 1 | 3 | S |
| Ferrioxamines | 1 | 2 | O, T, V, F, S |
| Rhodotorulic acid | 1 | 2 | O, T, V, F, S |
| Microbial cellulose | 1 | 2 | O, T, V, F, S |
| Celluloses | 2 | 1 | O, T, V, F, S |
| Deferoxamines | 1 | 1 | O, T, V, F, S |
| Deferasiroxamine B | 1 | 1 | O, T, V, F, S |
| EDTA | 1 | 1 | O, T, V, F, S |
| EGTA | 1 | 2 | T, V, F, S |

TABLE 1-continued

CHELATORS THAT MAY BE USED IN COMBINATION WITH BASE AGENTS

| CHELATOR | POTENCY^ | CONSUMABLE | ANTICIPATED USE* |
|---|---|---|---|
| Chlorophylls | 1 | 2 | O, T, V, F, S |
| DMSA | 1 | 2 | T, V, F, S |
| DMPS | 1 | 2 | T, V, F, S |
| Vitamin B12 | 1 | 1 | O, T, V, F, S |
| Cyclodextrins | 1 | 1 | O, T, V, F, S |

^Score 1-3. 1, most; 2, moderate; 3, least.
*O: oral administration, T: topical administration, V: veterinary, F: food safety, S: surfaces.

TABLE 2

BASE AGENTS THAT MAY BE USED IN COMBINATION WITH CHELATORS

| BASE | POTENCY^ | CONSUMABLE | ANTICIPATED USE* |
|---|---|---|---|
| Pyridoxine | 1 | 1 | O, T, V, F, S |
| Pyridoxal-5-phosphate | 1 | 1 | O, T, V, F, S |
| Vitamin K | 1 | 1 | O, T, V, F, S |
| Lysine | 2 | 1 | O, T, V, F, S |
| Arginine | 2 | 1 | O, T, V, F, S |
| Uracil | 3 | 1 | O, T, V, F, S |
| Lysozyme | 1 | 2 | O, T, V, F, S |
| Tris amine | 2 | 3 | T, V, F, S |
| Tris (hydroxymethyl) amine | 2 | 3 | T, V, F, S |
| Sodium bicarbonate | 3 | 1 | O, T, V, F, S |
| protamine sulfate | 2 | 3 | O, T, V, F, S |
| D-maltose | 1 | 1 | O, T, V, F, S |
| A-galactase | 1 | 1 | O, T, V, F, S |
| Remitidine | 1 | 1 | O, T, V, F, S |
| Omeprazole | 1 | 1 | O, T, V, F, S |
| Famotidine | 1 | 1 | O, T, V, F, S |
| Diethylamine | 2 | 3 | F, S |
| Sodium phosphate forms | 3 | 1 | O, T, V, F, S |
| Dibasic calcium phosphate | 3 | 1 | O, T, V, F, S |
| Vitamin B12 | 2 | 1 | O, T, V, F, S |
| Sodium hydroxide | 1 | 2 | O, T, V, F, S |
| Potassium hydroxide | 1 | 2 | O, T, V, F, S |
| Pyridoxamine | 1 | 1 | O, T, V, F, S |

^Score 1-3. 1, most; 2, moderate; 3, least.
*O: oral administration, T: topical administration, V: veterinary, F: food safety, S: surfaces.

Additionally, methods of selecting base, chelator and enhancers for a composition may be determined experimentally by administering a concentration or concentration range of agents to microbes, contaminated surfaces, animal models and/or mammalian cells to achieve a desired outcome. In some embodiments, compositions may be administered to a commensal microbe such as *Lactobacillus acidophilus*, a pathogenic microbe such as *Streptrococcus mutans*, and human biofilms and may be assessed for efficacy. In some embodiments, compositions may be administered to a mammal or to mammalian cells and the effect of a composition may be evaluated for efficacy. In some applications, compositions may be selected for having optimal anti-pathogen effects with minimal affect to commensal microbes. In some applications, compositions may be selected for having optimal anti-biofilm efficacy. In some applications, compositions may be selected for having optimal anti-growth efficacy. In other applications, compositions may be selected for having optimal effects on microbial metabolism. Yet in other applications, compositions may be selected for having optimal activity against microbe-mediated inflammation.

Additionally, methods for selecting appropriate chelator and base combinations may be achieved through the use of a test. A test may be conducted to identify and quantify parameters such as; pH; sugar content; protein content; the presence of pathogens and/or pathogenic molecules; the presence and/or level of metabolites such as nitrites, nitrates, sulfates, volatile aromatic compounds; the presence and/or level of inflammatory mediators; and others. Methods may relate to conducting a test to identify an optimal composition for use in a specific indication. Methods may also relate to conducting a test to determine the frequency in which composition may be used for optimal results. Methods may also relate to testing frequency to monitor the efficacy of a selected composition and its efficacy over time. Methods may relate to sampling a patient, mammal, or surface followed by performing one or more test on a sample. Methods also relate to performing one or more test in situ through the administration of a test article to a patient, mammal, or surface.

In some embodiments, any of the methods disclosed herein can comprise use of a pH test strip to measure the pH of a sample. Samples may comprise environmental, surfaces, saliva, crevicular fluid, urine, sweat, tears, sebaceous secretions, blood or other. In one embodiment, a test may be conducted using a pH test strip to measure the pH of a sample to help guide the selection of an optimal base and chelator composition. In one embodiment, a test may be conducted using a pH test strip to measure the pH of a sample to help guide the dose, frequency of administration or other of a composition. In one embodiment, a test may be conducted using a pH test strip to measure the pH of a sample to measure the change in pH following administration of a composition and thus may be used to test the efficacy of a composition.

In some embodiments, any of the methods disclosed herein can comprise use of stains to test for the presence or burden of microbes, microbial biofilm, microbial metabolite, microbial effector or inflammation. In some embodiments, a test may be conducted using a dextran-staining dye to measure the presence and abundance of biofilm in a sample or on a surface; may be used to help guide the selection of an optimal base and chelator composition; may be used to assess burden and may be to help guide the dose of composition to be administered; the frequency of administration or may be used to measure the change in biofilm burden following administration of a composition and thus may be used to test the efficacy of a composition.

Other non-limiting examples of tests relate to the use of immunoassays to detect and quantify the amount of a specific analyte in a sample. In some embodiments, immunoassay tests may be approved for use in the diagnosis of a microbial-related inflammatory disease. Examples of analytes to be measured may comprise: pathogen markers, metabolic markers, microbial effectors, toxins and inflammatory markers such as inflammatory cytokines, chemokines, antigen-specific IgG, IgA, IgM and IgE, and leukocyte esterase and other immune-related enzymes. In some embodiments, test results may be used to help guide the selection of an optimal base and chelator composition; may be used to assess disease severity and may be to help guide the dose of composition to be administered; the frequency of administration or may be used to measure the change in disease status following administration of a composition and thus may be used to test the efficacy of a composition.

Yet other non-limiting examples of tests relate to the use of chemical tests to detect and quantify the amount of specific analyte in a sample. In some embodiments, chemical tests may be approved for use in the diagnosis of a microbial-related inflammatory disease. Examples of analytes to be measured comprise glucose, nitrite, nitrate, sulfite, sulfate, aromatic volatile compounds or other. In some embodiments, test results may be used to help guide the selection of an optimal base and chelator composition; may be used to assess disease severity and may be to help guide the dose of composition to be administered; the frequency of administration or may be used to measure the change in disease status following administration of a composition and thus may be used to test the efficacy of a composition.

EXAMPLES

Example 1. Compositions to Affect Microbial Growth

Figure 5A:
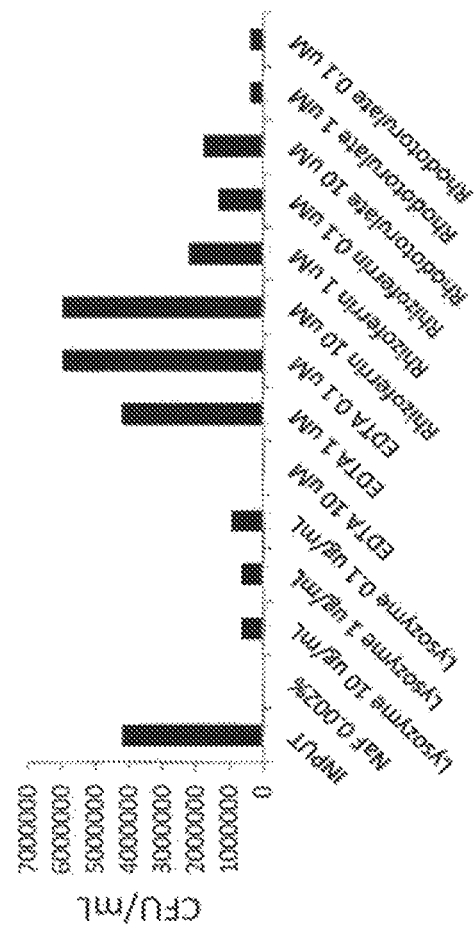
FIGS. 5A and 5B depict an exemplary differential effect on pathogenic and commensal microbes.
Figure 5B:
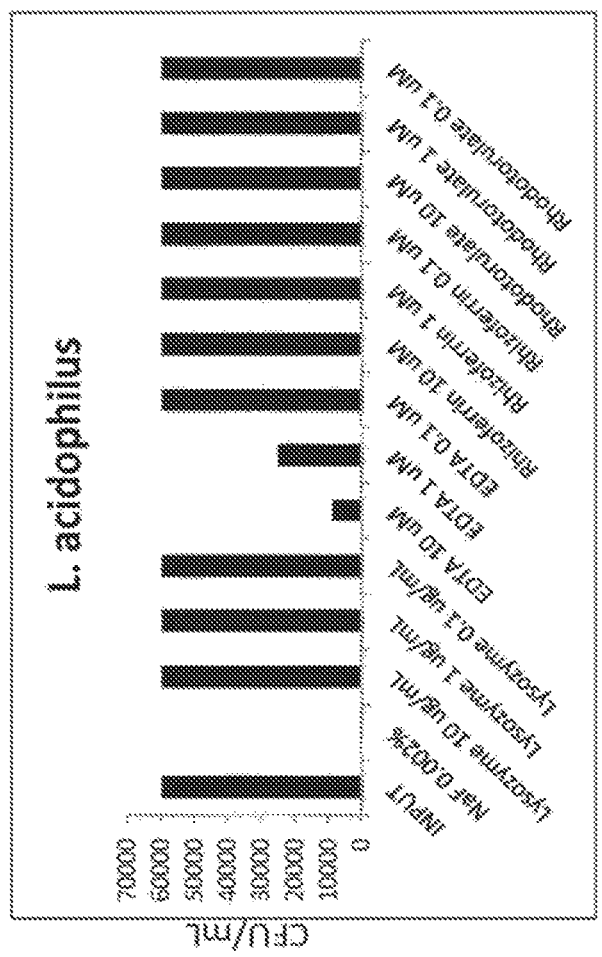
Figure 6:
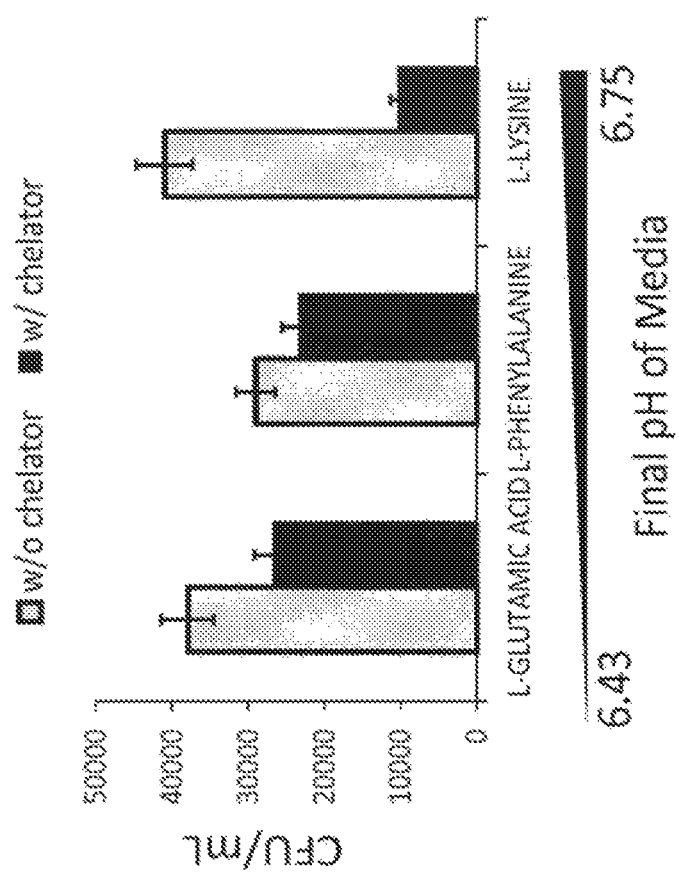
FIG. 6 depicts an exemplary effect of chelator and basicity of agents on microbial growth.

Compositions comprising chelator and base can affect microbial growth. It was discovered that the administration of compositions comprising chelator and base inhibit pathogen growth in a biofilm. Static cultures of pathogen *S. mutans*, commensal *L. acidophilus* (purchased from ATCC) or complex biofilms isolated from human dental plaque by sterile swab and were grown for 24-72 h in polystyrene microtiter plates and allowed to form biofilms. Wells were treated briefly with compositions or controls prior to repletion with sterile media (RPMI, pH 7.2) and their effects on pathogen growth was then evaluated using standard microbiological methods for plating and counting colony forming units (CFUs) on TSA plates (FIGS. 1, 5-6). Optimal microbial growth-interrupting compositions were identified for each pathogen and for the microbes residing in the donor plaque by screening chelator, base and enhancer agents at various concentrations and combinations.

An amino acid may be used in combination with a chelator to affect microbial growth. The more basic a side chain is (at neutral pH) on an amino acid, the more potential growth affecting potential exists when used in combination with a chelator (FIG. 6). A chelator may be, for example, a siderophore such as rhodotorulic acid, rhizoferrin, azotobactin, ferrichrome, desferrioxamine B, bacillibactin, and others. In some embodiments, a chelator may be plant-derived such as pectin, carboxymethylcellulose, cellulose, cyclodextrin and others.

Furthermore, it was discovered that the administration of compositions comprising chelator and base can inhibit the growth of pathogens in established biofilms. Briefly, microbial biofilm was harvested from human mucosal and dermal surfaces and cultured in 96-well flat-bottom polystyrene microtiter plates and spiked with ~$10^3$ CFU of pathogen. Pathogen-containing biofilms were briefly exposed to saline control or compositions and were then repleated with RPMI media, pH 7.2. Pathogen growth in saline-treated biofilms was compared to pathogen growth in composition-treated biofilms. Pathogens were recovered from treatment samples by serial dilution in sterile saline followed by plating on TSA blood agar plates. Recovered CFUs were tabulated. Exemplary data are presented in FIG. 6 and demonstrate that the application of chelator and base compositions can be effective at limiting the growth of pathogens, even in the presence of a protective biofilm.

Example 2. Compositions to Affect Biofilms

Compositions comprising chelator and base can affect biofilm formation, development, composition and/or integrity. Microbial biofilms are linked to persistent infection, chronic inflammation and chronic diseases. Clearance or containment of microbial biofilms is important and there are limited compounds capable of killing pathogens that reside in biofilms due to poor penetration and/or slow kinetics of antibiotics into biofilms, enabling pathogen survival and disease persistence despite the presence of many antibiotics and antiseptics on the market (Brown et al. (1988) *J Antimicrob Chemother.* 22:777-780; Lewis K. (2001) *Antimicrob Agents Chemother.* 45:999-1007).

Figure 2:
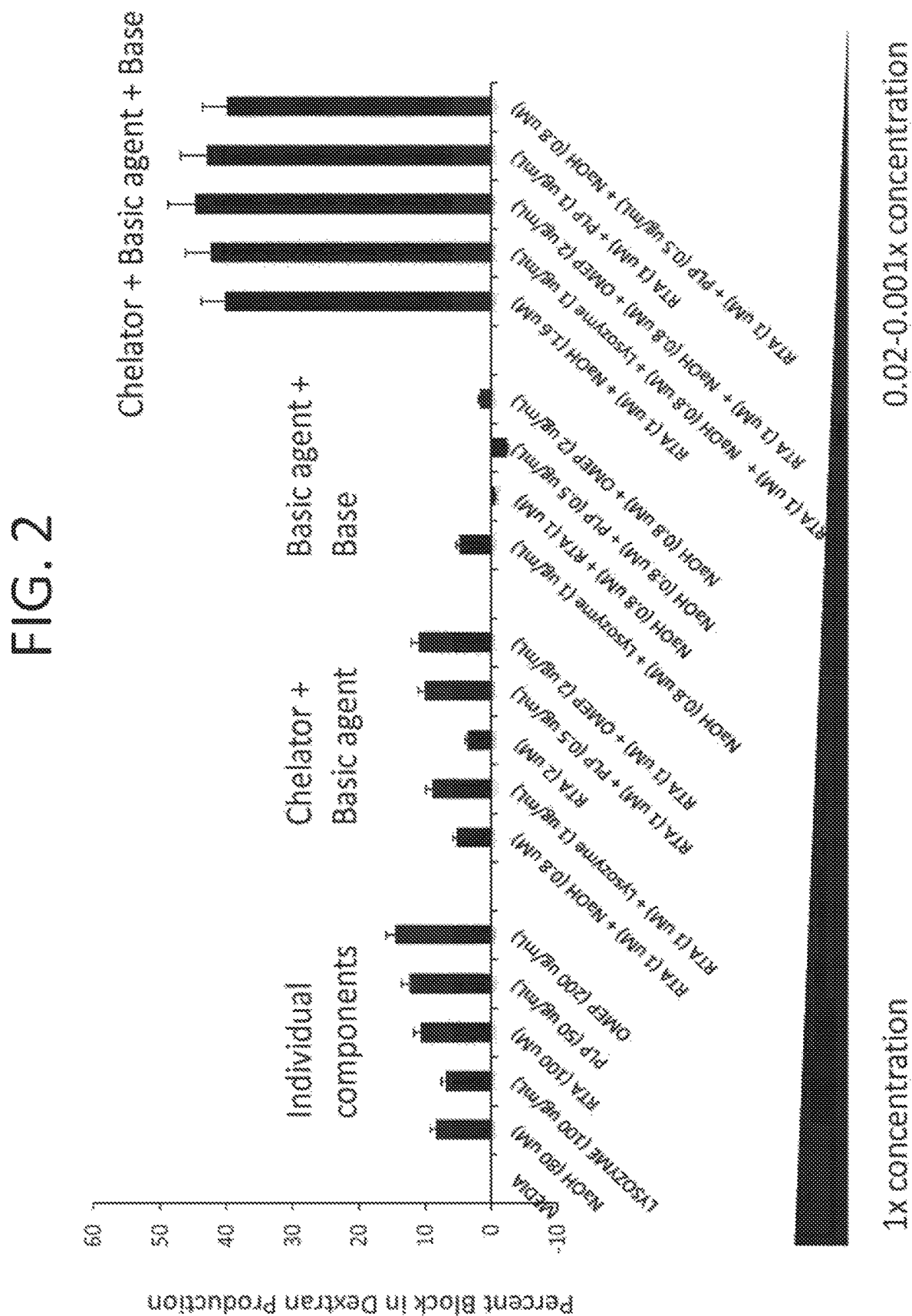
FIG. 2 depicts the effect of individual agents vs. synergistic effect of agent combinations on biofilms.
Figure 3:
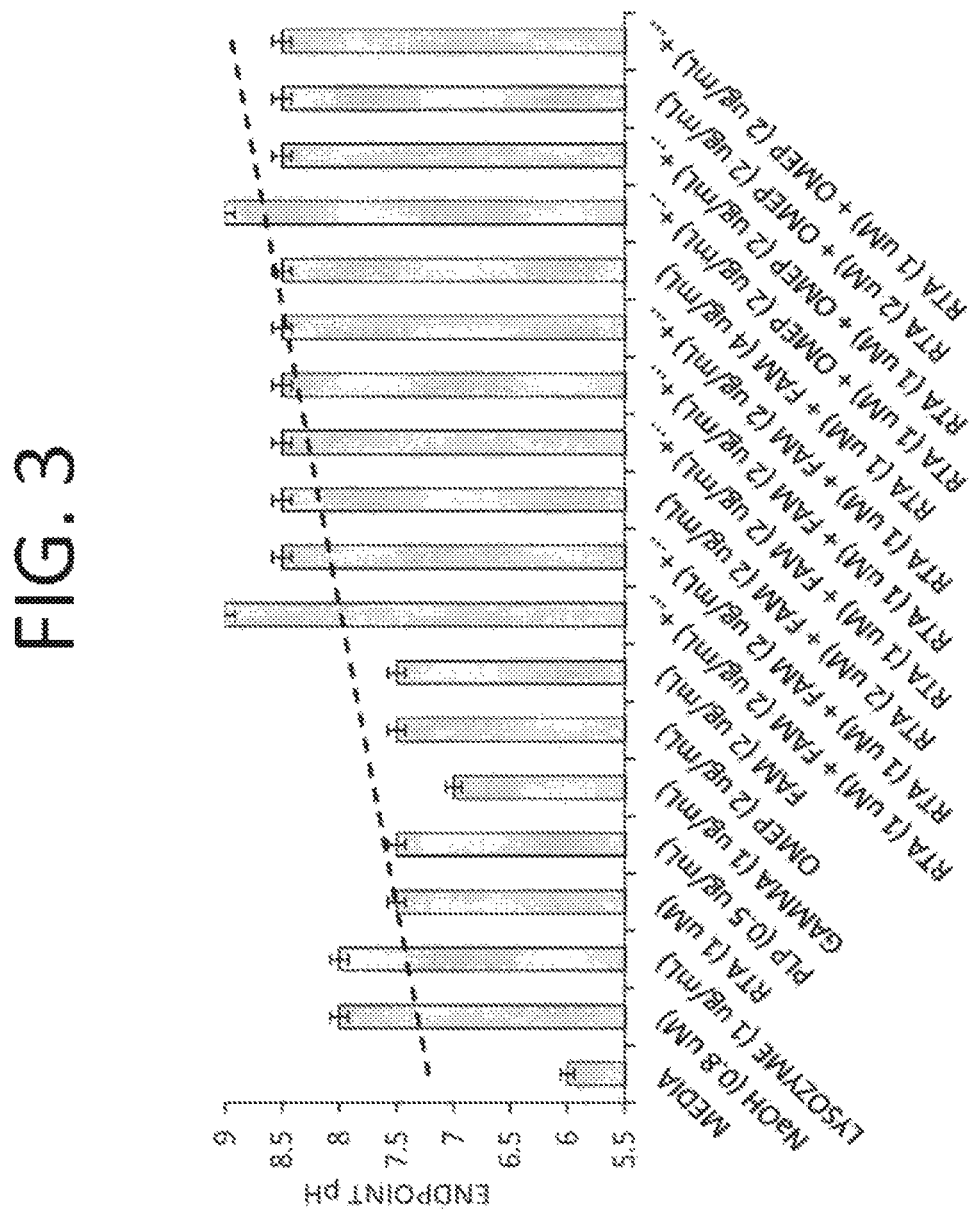
FIG. 3 depicts the effect of individual agents vs. agent combinations on microbial acid production.

Microbes were cultured in growth media and plated at $10^3$ CFU/well in a 96 well microtiter plate and cultured for 24 h. Wells were then treated with 10-50 μL of media only as control or with media+chelator agents, base agents, acid agents, neutral agents or enhancer agents for 30 min at RT followed by repleation in 0.100 μL of fresh RPMI pH 7.2. Plates were then incubated for an additional 48-72 h prior to harvest. Wells were washed 3× in PBS and residual biofilm was stained using crystal violet. Wells were washed 4× in PBS and the amount of retained stain was measured. It was initially determined that strong base alone may inhibit biofilms, however, strong base is toxic to most organisms and such caustic compounds are not meant for frequent exposure. Unexpectedly, it was observed that biofilms were inhibited by the administration of a chelator at pH of 7.0-8.0 (human physiologic pH), but not below pH 6.8. Furthermore, it was determined that low concentrations of base (0.8-1.6 μM) in the presence of low concentrations of chelator (1 μM) is superior to higher concentrations of base (50 μM) or higher concentrations of chelator (100 μM) alone in blocking biofilms. Synergistic effects were evaluated and numerous compounds were examined for their ability to synergistically act with chelators to inhibit biofilm formation (examples of some test compounds analyzed for synergy with chelators are presented in Table 2). An example of screening results is presented in FIG. 2. Additional dose titrations studies were performed for select compounds (examples of dose titration am presented in FIG. 3). It was discovered that compositions comprising low concentrations of chelator and base, or compositions comprising low concentrations of chelator, base and enhancer, were significantly more effective than higher doses of the individual agents (FIGS. 1-3). These data present some examples of chelator and base compositions having biofilm affecting activity. These data also present some examples of chelator and base compositions that may be used to inhibit biofilm formation, development, composition and/or integrity.

Example 3. Compositions to Affect Microbial Metabolism

Compositions comprising chelator and base can affect microbial metabolism. Many microbes undergo metabolic processes that generate acidic waste products, many of which are secreted into the surrounding environment. Sugar fermentation is a metabolic process whereby carbohydrates are converted into lactic acid, acetic acid or other acids. Examples where microbial acid production and its secretion into the surrounding environment have undesired consequences are demineralization of tooth enamel, metabolic disruption of neighboring mammalian cells (acid erosion of the gums, skin flaking on the scalp (also known as dandruff)), immune cell activation, cancer and others.

It was initially determined that biofilm production can be disrupted by the administration of a chelator under basic conditions, but not under acidic conditions (FIG. 2). Using similar microtiter plate based approach, oral commensals and oral pathogens were cultured in RPMI pH 7.2 and were briefly exposed to single base or chelator agents or combinations of bases and chelators. Assessment of metabolic output 24, 48 and 72 hr post-treatment was measured. pH was determined using the acid-sensitive dye Phenol Red to measure acid production in each well, with secondary testing using a pH test strip (pHion and Seimens). Microbial metabolism was also assessed by Multistix 10 SG strips for glucose, nitrite, ketones, protein and other parameters (Siemens). It was also determined that low concentration of chelator can inhibit acid production by the cariogenic pathogen *S. mutans* in the presence of base, which significantly increases as increasing base concentrations are present (data not shown). It was also discovered that compositions of chelator and base can disrupt the ability of *S. mutans* to maintain homeostatic pH function, as the optimal pH for *S. mutans* growth and biofilm formation was determined to be pH 6.5, which is also near the average pH of human saliva. For example, at pH input 6.5, the endpoint pH was observed to be 8.5; at pH input 8, the endpoint pH was observed to be 8.5 (data not shown).

Furthermore, it was determined that low concentrations of base may alter the endpoint pH of *S. mutans* cultures. Screens of base components to use in compositions comprising chelator were performed. Examples of base components screened are presented in Table 2 and FIG. 3. Briefly, the pH of *S. mutans* cultures were measured 24 and 48 hr post administration of chelator and candidate base components. Combinations of chelator, base and enhancer agents were also evaluated for affecting metabolic activity and/or metabolism of *S. mutans* (FIG. 3). It was also determined that low concentrations of base (1×) in the presence of low concentrations of chelator (1×) were superior to higher concentrations (2×) of base or chelator alone (data not shown). Synergistic effects on microbial acid production were observed. These data teach that chelator and base may be administered to biologic and inanimate surfaces to limit acid production of the microbes inhabiting them.

Example 4. Compositions and Formulations to Promote Oral Health

Compositions comprising chelator and base can promote oral health. Many microbial metabolic products have beneficial effects for mammals (examples are fermented foods and beverages). Many other microbial metabolic products have pathogenic effects on mammals (Ramsey et al. (2011) *PLOS Pathogens*). It was observed that *S. mutans*-specific dextran production was enhanced in the presence of chelator at pH 5.5 to 6.5 (data not shown). It is also observed that *S. mutans*-specific dextran production can be inhibited when a chelator is administered with a base (FIG. 2). It is also observed that the administration of compositions comprising chelator and base can affect microbial metabolism, namely acid production (FIG. 3). Synergistic blockade of microbial dextran production and acid production may be important for the prevention of oral pathology such as gingivitis, gum erosion, enamel loss, cavities, periodontitis, mucosal inflammation and others.

In some examples, chelator and base compositions can be formulated in a liquid or solid form and can be administered to mammals to inhibit microbial effectors such as acid, biofilm production, overgrowth and related inflammation. An example of results obtained from oral administration of liquid composition (from about 1 to 3 mL) comprising water, chelator (gamma-cyclodextrin, 10 μg/mL), base (sodium hydroxide, 10 ng/mL) and flavoring agent (cinnamon extract) to human volunteers is presented in FIG. 4A. Subjects were sampled at intervals over about a 12-hour period for salivary pH, protein content and glucose concentration. Subject salivary samples were measured prior to administration and at 30 mins following administration. The liquid composition was ingested in this example as the composition is non-toxic and meant for consumption. Testing was performed using test strips (Multistix, Siemens). Differences in pH, protein content and glucose levels were observed in all subjects.

Figures 4A, 4B:
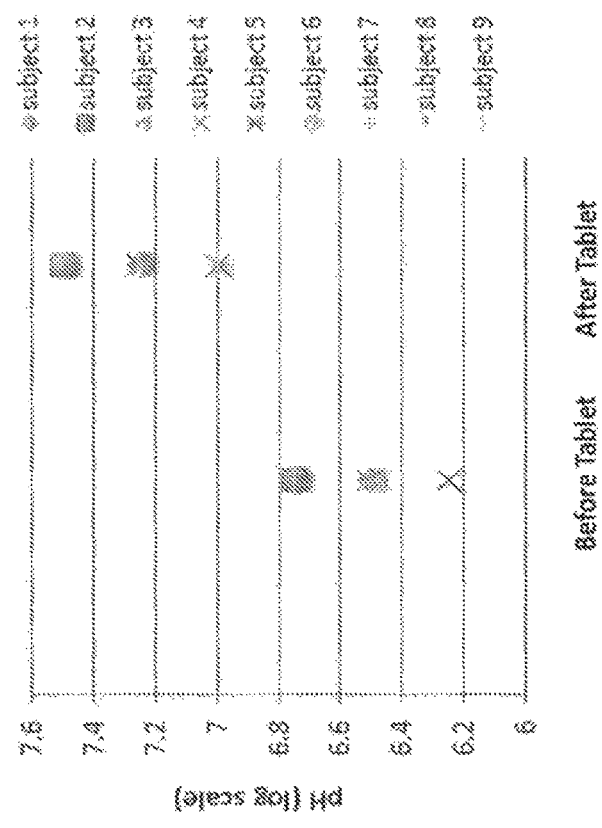
FIGS. 4A and 4B depict the effect of compositions and formulations on human oral health markers.

An example of results obtained from oral administration of rapid melt tablet compositions (ranging from about 320 to about 350 mgs per tablet) comprising filler (in some non-limiting examples, xylitol, sorbitol, Stevia or mannitol was used, ranging from about 310 to about 345 mgs per tablet), chelator (alpha-cyclodextrin, ranging from about 5 to about 30 µg per table), base (pyridoxal-5-phosphate, ranging from about 0.5 to about 15 µg per tablet), enhancer (sodium bicarbonate, ranging from about 0.3 to about 12 µg per tablet), and flavoring agent (peppermint) to human subjects is presented in FIG. 4B. Subject salivary samples were assessed for pH using pH test strip prior to tablet administration and at 30 mins following tablet administration. Differences in pH were observed in all subjects. These data teach that formulations comprising chelator and base compositions can be administered to affect microbial metabolism, reduce pathology-inducing effects and promote oral health.

Example 5, Compositions to Selectively Affect Pathogens Over Commensals

Compositions comprising chelator and base can selectively affect pathogens over commensal microbes of a mammal's microbiota. The adult human gut contains up to 100 trillion microbial organisms and all mucosal and dermal surfaces of mammals comprise microbes, known as the microbiota of a mammalian host. Specific strains of bacteria have been implicated in the disease pathogenesis of cancer, oral diseases, cardiovascular diseases, diseases of the central nervous system, metabolic diseases and systemic diseases. *Streptococcus*, *Bacteroides*, *Clostridia*, and *Helicobacter* species are a few of many microbes having been implicated in disease. Conversely, some microbes, including *Lactobacillus acidophilus* and *Bifidobacterium longum*, have been shown to be protective against certain diseases. Thus, the balance between "detrimental" microbes (referred to herein as pathogens) and "beneficial" microbes (referred to herein as commensals) may have implications for disease risk, progression and/or severity in mammals. Non-limiting examples of select chelator and base agents that can be used in compositions to selectively affect pathogens without adversely affecting commensals are presented in FIG. 5.

Example 6. Health-Promoting Compositions and Formulations

Compositions comprising chelator and base can be administered for promoting and maintaining health. Compositions may be formulated in a solid dosing form such as tablet, capsule, powder, crystalline, gum, thin strip, lozenge, patch, or other. Solid dosing formulations may comprise plasticizer, polymer, filling agent, sweetening agent, coloring agent or flavoring agent. Compositions may be formulated in time-release dosing forms.

Solid dosing formulations may be administered frequently or on an as needed basis and may be packaged in a single dose, a multi-dose pack, or other. Formulations may be administered orally for sublingual absorption or may be ingested for absorption in the stomach or intestine. Formulations may also be administered dermally in a patch for absorption by the skin.

Compositions may also be formulated in a liquid dosing form such as liquid, solution, suspension, emulsion, gel, creme, lotion, serum, elixir, or other. Liquid dosing formulations may comprise plasticizer, polymer, filler, sweetening agent, coloring agent, flavoring agent, fragrance, inhalant, evaporant or other. Compositions may be formulated in time-release dosing forms and may comprise nanoparticles, microparticles, or crystals.

Liquid dosing formulations may be administered frequently or on an as needed basis and may be packaged in a single dose, multi-dose pack, concentrate or other. Formulations may be administered: for oral absorption in the mouth or gut; absorption by the skin; aerosolized or nebulized for absorption by the nasal and sinus cavities or by the lungs; rectally for absorption by the gut; for absorption by the eye; in the genitourinary tract; or for absorption by the ear.

Example 7. Administration of Compositions Following Consumption of Sugar- and Acid-Containing Foods and Beverages Compositions comprising chelator and base can be administered orally for promoting and maintaining health following consumption of foods and beverages that promote microbial growth, undesirable microbial metabolism, or inflammation. Compositions may be formulated in a direct dose or may be formulated in a time-release formula. Compositions may be formulated in liquid or solid dose forms for sublingual absorption or absorption by the stomach or intestine. Compositions may be administered on an as needed basis following consumption of food or beverage.

Example 8, Compositions for Topical Administration

Compositions comprising chelator and base can be used for topical administration to affect microbial biofilm, microbe-specific metabolism and inflammation of the skin. Human skin is a complex organ that protects and regulates the interaction with the external environment. Microbial biofilms permanently inhabit the epidermis with transient microbes that occur through contact-mediated transmission. The topical microbial flora is composed primarily of Gram-positive bacteria and fungus. Topical infections often result from injury to the skin, which provides access of microbial biofilms to the underlying tissue. Large bacterial populations in wounds have been correlated with delayed healing, and control of microbial infection is recognized as an important aspect of wound care (Seth et al. (2012) *PLoS One* 7:e42897).

Skin-residing microbial biofilms have also been strongly associated with acne and dandruff. *Propionibacterium acnes* and *Staphylococcus epidermidis*, in addition to approximately 16 other bacterial species constitute the follicular microbiome (Bek-Thomsen et al. (2008) J Clin Microbiol. 46:3355-3360). Over 85% of the population has been afflicted by this disease, which accounts for more than 14 million acne-related clinical visits per year in the United States. Data also suggest that acne may contribute to significant psychological distress, depression and even increased risk of suicide in teenagers suffering from severe acne (Mancini A J. (2008) Johns Hopkins Adv Stud in Med. 8:100-105; Hanisah et al. (2009) J Prim Healthcare. 1:20-25).

An example of a composition to limit the fungal burden residing on the human scalp is presented in FIG. 7. As exemplified in FIG. 7, fungus was sampled from human scalps using sterile swabs and cultured in Sabouraud liquid media (pH 5.4). Sensitivity to various compositions were tested using traditional microbiological culture methods (for example, Sabouraud-brain-heart infusion plates supplemented with chloramphenicol to inhibit bacterial growth). Compositions may be selected for one or more particular fungal species in a personalized manner. In other non-limiting examples, subjects were treated for 5 mins with control solution (10 mM NaCl) or various compositions (50 μL per donor) on the left wrist. Treatment zones were outlined on each subject by permanent marker prior to washing with sterile water. Treatment zones were then sampled by sterile swab and compared to sampling the untreated wrist (right wrist). Swabs were plated on Sabouraud-brain-heart infusion plates supplemented with chloramphenicol to inhibit bacterial growth and allowed to grow for 5 days. Fungal growth between treatment and control zones were assessed and tabulated. Results from these studies may be used to inform selection of a composition with desired effectiveness. Compositions may be formulated with detergents, surfactants, natural oils, coloring agents, fragrances, polymers, salts, waxes, emulsifiers, antioxidants, and moisturizers.

Compositions for topical administration may be formulated in washes, wipes, make-up, crémes, lotions, shampoos, conditioners, gels, mousse, sprays, deodorants or other.

Compositions may be applied to skin surfaces, followed by manual rubbing and massaging actions. Compositions may also be contacted to skin surfaces by spray, followed by manual rubbing and massaging actions. Yet in other methods, compositions may be applied to the skin, followed by removal of the compositions by rinsing. Topical compositions may be applied routinely in a single dose format or may be applied periodically throughout the day.

In some non-limiting examples, topical compositions may be used to reduce microbial burdens, to reduce microbial metabolic activity, to reduce metabolically-derived malodor on skin surfaces, and to reduce microbe-triggered inflammation of the skin.

Example 9. Composition for Affecting Malodor

Malodor is considered an aesthetic problem by many people worldwide. Considerable time and money is spent to limit odor due to inherent social and cultural biases. Current methods to affect malodor involve the application of "odor masking" technologies, such as deodorant and perfume. Other methods involve the application of "odor sequestration" technologies such as talcs and powders. Yet other methods involve the application of "antiperspirant" creams, pastes, solutions and others to block sweat and oil secretion by the skin, Here, we present compositions affecting microbe-mediated malodor. Mucosal and dermal malodor is known to arise from the metabolic activity microbes living on the skin and mucosal surfaces of a mammal. Malodor is produced by aromatic metabolic waste products generated from microbial metabolism. Commonly, commensal microbes use the secreted oils of the skin as carbon sources for energy production and use consumed food as carbon sources in the gut of the mammalian host. Aromatic waste products may include butyric acid, acetic acid, propionic acid, sulfites, volatile aromatic compounds and other. Chelator and base compositions may be formulated in a powder, creme, gel, solid, lotion, wash, gum, lozenge, tablet, capsule, liquid, gel, deodorant or wipe to inhibit microbe-mediated odor production. Compositions may be administered topically, orally, or rectally by manual application, through the use of a device such as a wipe. Compositions may be administered frequently on a daily basis or on an as needed basis.

Example 10. Health-Promoting Compositions for Surfaces

Compositions comprising chelator and base can be administered to food and surfaces to promote health. Pathogen-harboring microbial biofilm contamination of food is a significant problem, worldwide. Foodborne illness is not decreasing in occurrence despite improvements in food handling, food processing and food storage practices. Foodborne illness accounts for 48 million illnesses, 128.000 hospitalizations and 3,000 deaths each year in the United States (USDA). Every year in the US, millions of tons of chicken, beef and pork products are recalled due to potential food safety issues (CDC).

Figure 8A:
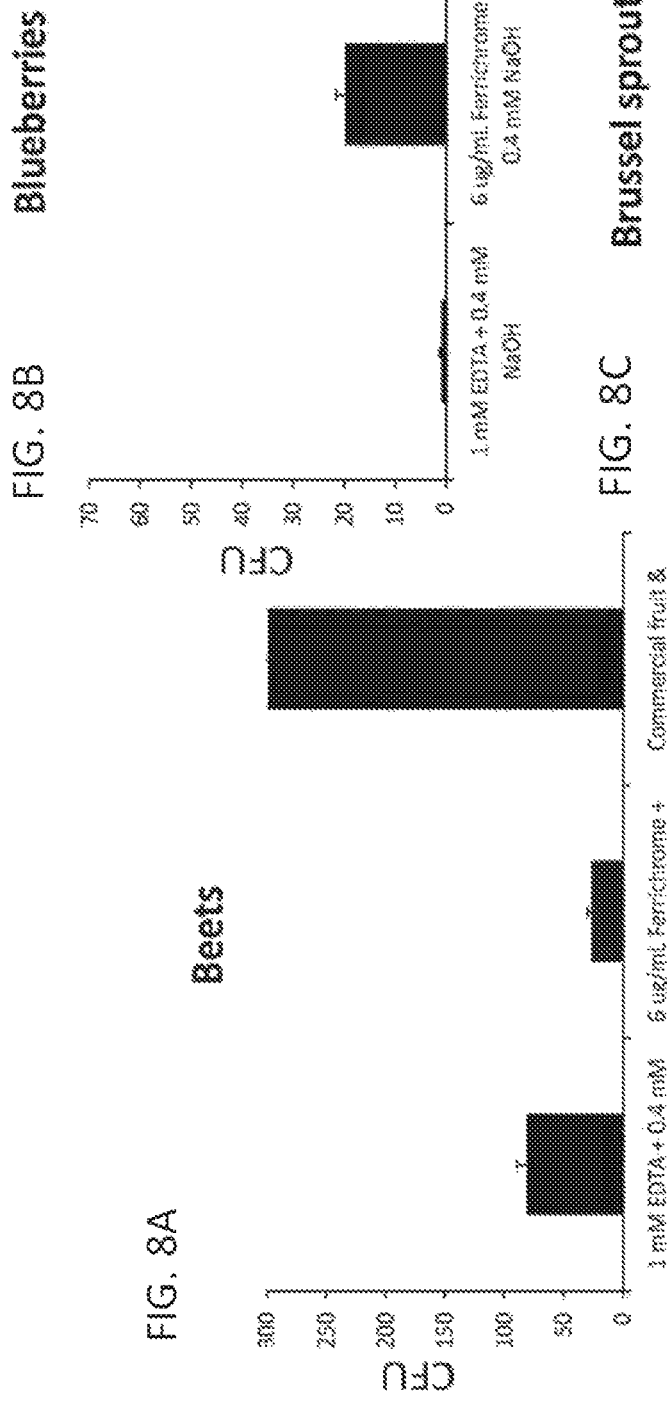
FIGS. 8A, 8B, and 8C depict an exemplary effect of chelator and base compositions on food biofilms.
Figure 8B:
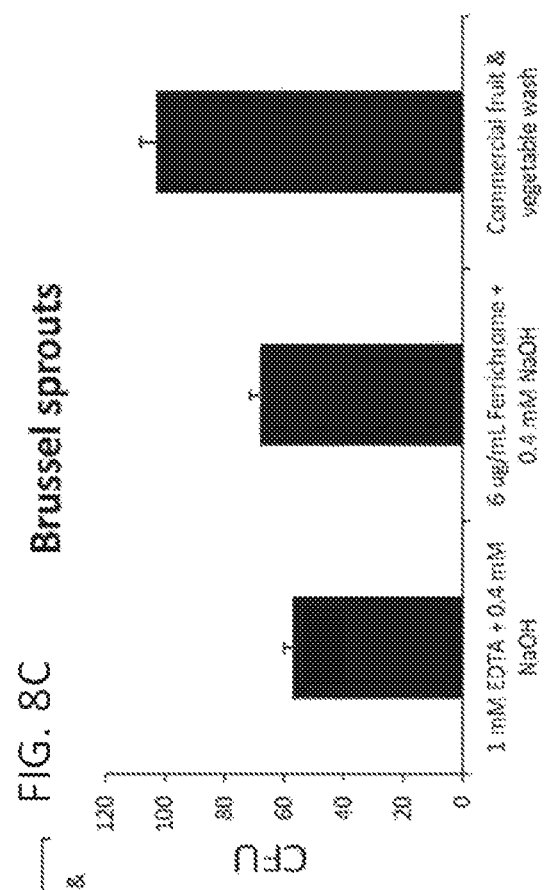
Figure 8C:
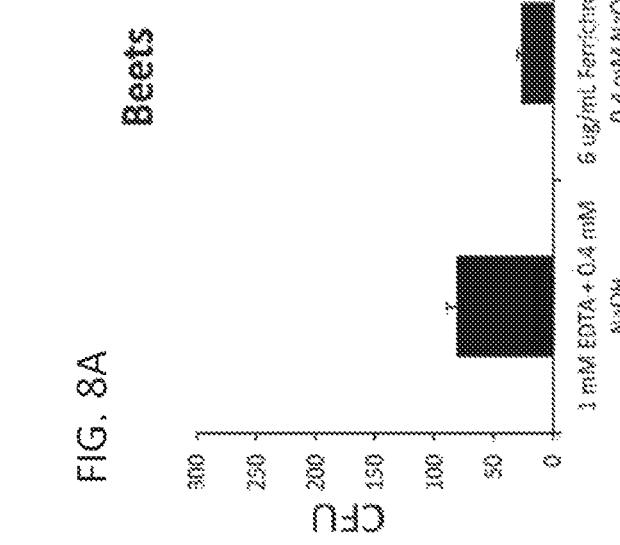

Compositions comprising chelator and base may be used for food safety. In some embodiments, compositions may be administered to the surface of foods to reduce the microbial CFU burden (examples are demonstrated in FIG. 8). In these embodiments, compositions or commercial vegetable wash was administered to fruits and vegetables for about 5 to 15 seconds and rinsed with tap water. Microbial CFU burden was evaluated using standard microbiologic techniques. Various chelator and base combinations were superior to commercial products and provide a safe, non-toxic and consumable method for promoting health.

Some compositions may be used as an additive in processed food and beverage and can be formulated in powders, liquids, gels, concentrates or other. Preferred methods of food safety compositions relate to the contacting of food and beverage during the course of preparation, processing and/or packaging said food and beverage.

Said food safety compositions may also be used as device surface treatments in food and beverage processing and preparation. Methods using food safety compositions relate to the administration of said composition to device surfaces that contact food during the course of processing and preparation. Methods may include the spraying of said composition to cutting blocks, conveyor belts, knives, forks, skewers, processing tools, processing machinery, packaging machinery and packaging materials.

Hospital-acquired (nosocomial) infections from contaminated devices or pathogen-carrying healthcare professionals results in incidental infections at a rate of approximately 4-5.5% in in-patient populations annually. The healthcare costs associated with biofilm contamination are estimated at $4.5 billion USD (Emori and Gaynes (1993) Clin Microbiol Rev. 6:428-442). Numerous approaches have been employed to reduce unnecessary exposure to pathogen-harboring biofilms, however, there remains an urgent need for novel and cost-effective approaches to prevent biofilm-associated illness through the administration of anti-microbial sprays, washes and additives.

Compositions comprising chelator and base may be used on biologic and inanimate surfaces as general cleaners to promote health. Exemplary surfaces may include doorknobs, keyboards, remote controls, cell phones, handles, elevator buttons, floors, counters, faucets, tools and others.

Compositions for administration to surfaces may be formulated as powders, gels, foams and liquids. Methods of administering compositions relate to the contacting of surfaces with the composition for a desirable period of time to disinfect, cleanse, or treat contaminated surfaces.

Example 11. Method of Testing Followed by the Selection of Desirable Health-Promoting Chelator and Base Composition Test methods to measure indicators of microbe-mediated inflammation, unwanted microbial metabolism, biofilm, or microbial overgrowth in a mammal may relate to the use of one or more test to measure the pH, nitrate level, protein content, leukocyte esterase level, cytokine level, dextran content of a sample or a surface. Test may be utilized on a routine basis, daily, weekly, monthly or on an as needed basis. The use test may aid in the: selection of health-promoting composition, determination of dose, dose form, formulation, frequency of use, route of administration and effectiveness.

Test methods may include the administration of a dye to stain surfaces or samples suspected of having evidence of microbe-mediated inflammation, unwanted microbial metabolism, biofilm, or microbial overgrowth. Dye stains may comprise commercial formulations including but not limited to dextran-binding dyes, hematoxylin and eosin, immunohistochemical stains, nitrite- or nitrate-sensitive dyes, protein dyes, sulfur-sensitive dyes and other. Test methods may also include the use of a test strip, lateral flow test, standard sandwich immunoassay, flow cytometric or other methods.

The examples, which are intended to be purely exemplary of the invention and should therefore not be considered to limit the invention in any way, also describe and detail aspects and embodiments of the invention discussed above. The foregoing examples and detailed description are offered by way of illustration and not by way of limitation. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A composition comprising a chelator and a base, wherein the chelator and base provide anti-inflammatory and microbial affecting activity;
   wherein the chelator comprises a cyclodextrin selected from the group consisting of alpha-cyclodextrin, beta-cyclodextrin, gamma-cyclodextrin, and methyl-beta-cyclodextrin; and the concentration of the chelator is between 0.1 nM and 500 mM per dose; and
   wherein the base comprises a basic amino acid selected from the group consisting of arginine, lysine, and histidine; and the concentration of base is between 750 pM and 250 mM per dose.

2. The composition of claim 1, wherein the base further comprises KOH, NaOH, pyridoxal-5-phosphate, pyridoxamine, pyridoxine, vitamin K, lysozyme, alpha-galactase, tris amine, sodium bicarbonate, or protamine sulfate.

3. The composition of claim 1, wherein more than one base is used.

4. The composition of claim 1, further comprising an enhancer.

5. The composition of claim 4, wherein the enhancer is proline, phenylalanine, or omeprazole and the concentration is between 0.0001% and 10% of the composition.

6. The composition of claim 1, wherein the composition is for use on a dermal surface.

7. The composition of claim 1, wherein the base further comprises sodium bicarbonate, or pyridoxal-5-phosphate and the chelator comprises alpha-cyclodextrin.

8. The composition of claim 1, wherein the composition is formulated as a créme, gel, lotion, spray, solution patch, solution, suspension, or a concentrate.

9. A method of promoting and maintaining health in a mammal comprising administering the composition of claim 1 to the mammal, wherein the composition is used to promote skin health, to promote wound care, or to treat or prevent infection, psoriasis, or acne.

10. The method of claim 9, wherein said method is repeated on a daily, monthly, quarterly or annual basis.

11. The method of claim 9, wherein the composition is formulated for topical administration to affect gram positive bacteria or fungus on the skin of the mammal.

12. The composition of claim 1, wherein the base comprises arginine.

13. The composition of claim 1, wherein the base comprises lysine.

14. The composition of claim 1, wherein the base comprises histidine.

15. The composition of claim 1, wherein the cyclodextrin comprises alpha-cyclodextrin.

16. The composition of claim 1, wherein the cyclodextrin comprises beta-cyclodextrin.

17. The composition of claim 1, wherein the cyclodextrin comprises gamma-cyclodextrin.

18. The composition of claim 1, wherein the cyclodextrin comprises methyl-beta-cyclodextrin.

19. The method of claim 11, wherein the gram positive bacteria is *Propionibacterium acnes* or *Staphylococcus epidermidis*.

* * * * *